US008050519B2

(12) United States Patent
Katsumata et al.

(10) Patent No.: US 8,050,519 B2
(45) Date of Patent: Nov. 1, 2011

(54) IMAGE COMBINING APPARATUS

(75) Inventors: Masaya Katsumata, Kanagawa (JP); Osamu Konno, Saitama (JP)

(73) Assignee: Olympus Corporation, Tokyo (JP)

( * ) Notice: Subject to any disclaimer, the term of this patent is extended or adjusted under 35 U.S.C. 154(b) by 1328 days.

(21) Appl. No.: 11/636,754

(22) Filed: Dec. 11, 2006

(65) Prior Publication Data

US 2007/0140539 A1    Jun. 21, 2007

(30) Foreign Application Priority Data

Dec. 19, 2005 (JP) .................................. 2005-365215

(51) Int. Cl.
*G06K 9/36* (2006.01)
(52) U.S. Cl. ....................................................... 382/284
(58) Field of Classification Search .................... 382/284
See application file for complete search history.

(56) References Cited

U.S. PATENT DOCUMENTS

| 5,619,588 | A  | * | 4/1997  | Yolles et al. ................. 382/149 |
| 5,986,771 | A  | * | 11/1999 | Henderson et al. ........... 358/448 |
| 6,008,905 | A  |   | 12/1999 | Breton et al. |
| 2001/0021271 | A1 | * | 9/2001  | Ishibashi ....................... 382/232 |
| 2002/0064750 | A1 |   | 5/2002  | Morris et al. |
| 2002/0126890 | A1 | * | 9/2002  | Katayama et al. ............ 382/154 |
| 2003/0190578 | A1 |   | 10/2003 | Lehmann |
| 2004/0136580 | A1 |   | 7/2004  | Matsumiya et al. |
| 2004/0252303 | A1 | * | 12/2004 | Giorgianni et al. ........... 356/402 |
| 2005/0062970 | A1 |   | 3/2005  | Delgrande et al. |
| 2005/0084826 | A1 | * | 4/2005  | Pilaro et al. ................... 433/215 |
| 2006/0114460 | A1 |   | 6/2006  | Boyer et al. |
| 2006/0192759 | A1 | * | 8/2006  | Adams et al. ................. 345/163 |
| 2006/0251408 | A1 |   | 11/2006 | Konno et al. |
| 2008/0137979 | A1 | * | 6/2008  | Perlmutter et al. ........... 382/255 |
| 2008/0277585 | A1 | * | 11/2008 | Hasegawa et al. ............ 250/334 |

FOREIGN PATENT DOCUMENTS

EP    1434028 A1    6/2004

(Continued)

OTHER PUBLICATIONS

U.S. Appl. No. 11/636,753, filed Dec. 11, 2006; Inventor: Masaya Katsumata, Title: Dental Colorimetry Apparatus.

(Continued)

*Primary Examiner* — Brian Werner
*Assistant Examiner* — Nirav G Patel
(74) *Attorney, Agent, or Firm* — Holtz, Holtz, Goodman & Chick, P.C.

(57) ABSTRACT

The color of a measurement object, such as a vital tooth, and the color of a comparison object to be compared with the measurement object are displayed to a user in an easily comparable manner. The invention provides an image combining apparatus including an image extracting unit for extracting an image of a vital tooth (hereinafter referred to as "measurement-object image") from a color image of the vital tooth and extracting an image of a shade guide (hereinafter referred to as "comparison-object image") from a color image of the shade guide, a combining-reference-line setting unit for setting combining reference lines on the measurement-object image and the comparison-object image, a combining unit for combining the measurement-object image and the comparison-object image to form a combined image, and a correction unit for correcting at least one of the measurement-object image and the comparison-object image so as to align their outlines on the combining reference line in the combined image when the outlines are not aligned.

20 Claims, 19 Drawing Sheets

FOREIGN PATENT DOCUMENTS

| | | |
|---|---|---|
| EP | 1486901 A2 | 12/2004 |
| GB | 2 365 648 A | 2/2002 |
| JP | 64-052455 A | 2/1989 |
| JP | 2001-299733 A | 3/2001 |
| JP | 2002-065707 A | 3/2002 |
| JP | 2003-303348 A | 10/2003 |
| JP | 2004-030158 A | 1/2004 |
| JP | 2004-506257 A | 2/2004 |
| JP | 2005-069807 A | 3/2005 |
| JP | 2005-130928 A | 5/2005 |
| JP | 2005-176915 A | 7/2005 |
| JP | 2005-201694 A | 7/2005 |
| JP | 3710802 B2 | 8/2005 |
| JP | 2005-532561 A | 10/2005 |
| JP | 2005-331488 A | 12/2005 |
| KR | 10-2005-0030200 A | 3/2005 |
| KR | 2005-30200 A | 3/2005 |
| WO | WO 02/12846 A1 | 2/2002 |
| WO | WO 03/036244 A1 | 5/2003 |
| WO | WO 2005/071372 A1 | 8/2005 |

OTHER PUBLICATIONS

Korean Office Action dated Oct. 30, 2009 issued in a counterpart Korean Application No. 10-2008-7014698.

* cited by examiner

FIG. 7

COMBINING REFERENCE LINE

☒ SHADE GUIDE
☐ VITAL TOOTH

☒ SHADE GUIDE
☐ VITAL TOOTH

☒ SHADE GUIDE
☐ VITAL TOOTH

☒ SHADE GUIDE
☐ VITAL TOOTH

☒ SHADE GUIDE
☐ VITAL TOOTH

☒ SHADE GUIDE
☐ VITAL TOOTH

IMAGE COMBINING APPARATUS

BACKGROUND OF THE INVENTION

1. Field of the Invention

The present invention relates to an image combining apparatus for combining a plurality of images. In particular, the present invention relates to an image combining apparatus, an image combining method, and an image combining program that are suitable for use in a colorimetry apparatus for performing colorimetry of teeth, skin, and so forth.

This application is based on Japanese Patent Application No. 2005-365215, the content of which is incorporated herein by reference.

2. Description of Related Art

In recent years, there has been increased interest in beauty and health. In the beauty industry, for example, whitening for reducing melanin pigment in the skin has become a fashionable unit in the pursuit of beauty.

Skin-diagnosis camera systems which are designed to allow observation of magnified images of the skin surface on a monitor are used in conventional skin diagnosis; for example, they are used in dermatology, aesthetic salons, beauty counseling, and so on. In the case of dermatology, for example, by observing images of the grooves and bumps in the skin, features of the skin surface can be diagnosed and counseling can be given.

In the field of dentistry, dental treatments such as ceramic crowns are another aspect of the pursuit of beauty. The procedure for applying ceramic crowns involves first preparing a crown (a prosthetic tooth crown made of ceramic) having a color that is close to the color of the patient's original tooth, and this crown is then overlaid on the patient's tooth.

Conventionally, crowns are prepared by the process described below.

First, in a dental clinic, a dentist or other person acquires an image of the oral cavity of a patient. More specifically, images of the whole oral cavity including a plurality of teeth, the surface of a patient's vital tooth used as a reference for the crown preparation, and the like are acquired.

Subsequently, from a plurality of tooth samples having different colors (hereinafter referred to as "shade guides"), the dentist selects a shade guide that is closest to the color of the patient's vital tooth (this procedure is referred to as a "shade take" below). The shade guides are, for example, tooth-shaped samples that are made of ceramics of a plurality of different colors.

Upon completion of the procedure described above, the dentist sends the acquired images and a specific identification number associated with the shade guide selected in the shade take to a dental laboratory that makes crowns. Then, the crown is produced in the dental laboratory on the basis of this information.

However, the shade take described above has a problem in that it is not entirely quantitative because it depends on the subjective judgment of the dentist. Also, the appearance of the shade guide and the patient's tooth color may differ depending on various factors, such as the color tone of the gums, the environmental conditions, the illumination (for example, the illumination direction and color), the level of fatigue of the dentist, and so on. Therefore, it is very difficult to select the optimal shade guide, which places a significant burden on the dentist.

Consequently, in order to reduce the above burden on the dentist or other person, apparatuses providing support in procedures such as the shade take have been proposed; in such apparatuses, for example, a shade guide that is closest to the color of the patient's vital tooth is automatically selected.

For example, Publication of Japanese Patent No. 3710802 discloses a technique including storing in a computer in advance a data table in which identification information data of a plurality of tooth reference colors corresponds to color information data of the tooth reference colors in the L*a*b* calorimetric system, inputting image data prepared by simultaneously acquiring a vital tooth and reference samples (corresponding to the above "shade guides") having the tooth reference colors, calculating a color correction value for substantially matching the color information data of the tooth reference colors of the reference samples in the L*a*b* calorimetric system analyzed in the image data with the color information data of tooth reference colors in the data table corresponding to the identification information data of the tooth reference colors to correct the color of the vital tooth, and extracting from the data table identification information data of a tooth reference color of color information data that corresponds to or that is similar to color information data of the corrected color of the vital tooth and outputting the extracted data.

However, in the invention disclosed in Publication of Japanese Patent No. 3710802, since the comparison results of the color of the vital tooth and the reference color etc. are expressed by numerical values, it is difficult for a user to intuitively understand the degree of color difference.

BRIEF SUMMARY OF THE INVENTION

An object of the present invention is to provide an image combining apparatus, an image combining method, and an image combining program in which a color of a measurement object, such as a vital tooth, and a color of a comparison object that is compared with the measurement object can be displayed to a user in an easily comparable manner.

According to a first aspect of the present invention, an image combining apparatus for forming an image by combining a first acquired image containing an image of a measurement object and a second acquired image containing an image of a comparison object to be compared with the measurement object includes an image extracting unit for extracting a measurement-object image from the first acquired image and extracting a comparison-object image from the second acquired image; a combining-reference-line setting unit for setting a combining reference line on each of the measurement-object image and the comparison-object image; a combining unit for combining the measurement-object image and the comparison-object image along the combining reference lines to form a combined image; and a correction unit for correcting at least one of the measurement-object image and the comparison-object image so as to align their outlines on the combining reference line in the combined image when the outlines are not aligned.

According to this configuration, the measurement-object image and the comparison-object image are, for example, joined and displayed as a single image. Therefore, the user can directly compare the colors of both images by viewing the boundary part of the joined area. Consequently, the user can also recognize a slight difference in color. In this case, even when the sizes of the measurement-object image and the comparison-object image are different and the outlines are not aligned in the combined image combined by the combining unit, correction is performed by the correction unit so as to align the outlines on the combining reference line. Accordingly, a natural combined image can be provided to the user.

The term "extracting" in the extracting unit includes not only the concept of extracting the measurement-object image from the first acquired image as a separate image, but also the concept of specifying the outline of the measurement-object image in the first acquired image. Regarding the comparison-object image, the term "extracting" includes the same concepts.

The method of "combining" described above is not particularly limited. For example, combining may be performed by joining image pieces cut along the combining reference line. Alternatively, images may be combined by overlapping images so as to make the combining reference lines set on the individual images align with each other, and varying the mutual transmittances on either side of the boundary of the combining reference lines.

The measurement object unit an object whose color is to be compared with that of a plurality of color samples that have different colors and that are prepared in advance. In addition to, for example, human body parts such as vital teeth, skin, and so on, other examples of the measurement object include interior furnishings such as curtains and carpets, leather goods such as bags and sofas, electronic components, and painted cars, walls, and so forth.

In the image combining apparatus, the combining-reference-line setting unit may set a line that passes through the center of gravity of the measurement-object image as the combining reference line on the measurement-object image and set a line that passes through the center of gravity of the comparison-object image as the combining reference line on the comparison-object image.

According to this configuration, in the measurement-object image and the comparison-object image, a line passing through the center of gravity of the image is set as the combining reference line. Consequently, the area ratio of both images in the combined image can be maintained so as to be substantially the same, and a balanced combined image can be provided.

In the image combining apparatus, the combining-reference-line setting unit may set the combining reference line at a position where the length of the measurement-object image in the vertical axis direction is the maximum on the measurement-object image along the vertical axis direction and set the combining reference line at a position where the length of the comparison-object image in the vertical axis direction is the maximum on the comparison-object image along the vertical axis direction.

According to this configuration, in the measurement-object image and the comparison-object image, each combining reference line is set along the vertical axis direction at a position where the length of the image in the vertical axis direction is the maximum. Accordingly, when the combining reference line is shifted by combining-reference-line shifting unit described below, the apparatus can easily follow this shift and a shifted combined image can be immediately formed.

The image combining apparatus may further include a combining-reference-line shifting unit for shifting the combining reference line in the combined image using an external device.

According to this configuration, the user can shift the combining reference line to a desired position. Accordingly, the area ratio of the measurement-object image to the comparison-object image in the combined image can be changed, and the position at which the color is compared can be freely changed.

When the combining reference line is shifted by the combining-reference-line shifting unit, the shifted combining reference line is not used without further processing and the combining reference line is reset on the measurement-object image and the comparison-object image on the basis of the combining reference line shifted by the user. Accordingly, the combining reference line can be set at an appropriate position in consideration of the total balance. As a result, the area ratio of both images in the shifted combined image can be maintained at a suitable value, and distortion of the outline can be reduced.

In the image combining apparatus, the correction unit may reduce or enlarge at least one of the measurement-object image and the comparison-object image.

According to this configuration, the outlines in the combined image can be aligned by simple correction processing.

In the image combining apparatus, for example, the measurement object may be a vital tooth and the comparison object may be a shade guide.

According to the present invention, a dental colorimetry system includes the image combining apparatus according to the first aspect of the invention, a chroma-value computing unit for computing chromaticity values near the combining reference line in the measurement-object image; a difference calculating unit for calculating the differences between the chromaticity values near the combining reference line of the measurement-object image and chromaticity values near the combining reference line of the comparison-object image; and a display control unit for displaying at least one of the chromaticity values near the combining reference line of the measurement-object image, the chromaticity values near the combining reference line of the comparison-object image, and the differences in the chromaticity values on a screen displaying the combined image.

According to this configuration, the user can understand the colorimetry information near the boundary as numerical values, as compared with the case where the user directly views the colors of the measurement object and the comparison object. Therefore, a subjective color comparison due to visual observation and an objective color comparison due to numerical values can be performed.

The image combining apparatus is particularly suitable for use in a dental colorimetry apparatus.

According to a second aspect of the present invention, an image combining method for forming an image by combining a first acquired image containing an image of a measurement object and a second acquired image containing an image of a comparison object to be compared with the measurement object includes an image extracting step of extracting a measurement-object image from the first acquired image and extracting a comparison-object image from the second acquired image; a combining-reference-line setting step of setting a combining reference line on each of the measurement-object image and the comparison-object image; a combining step of combining the measurement-object image and the comparison-object image along the combining reference lines to form a combined image; and a correction step of correcting at least one of the measurement-object image and the comparison-object image so as to align their outlines on the combining reference line in the combined image when the outlines are not aligned.

According to a third aspect of the present invention, in an image combining program for forming an image by combining a first acquired image containing an image of a measurement object and a second acquired image containing an image of a comparison object to be compared with the measurement object, the image combining program causes a computer to execute image extracting processing for extracting a measurement-object image from the first acquired image and extracting a comparison-object image from the second acquired image; combining-reference-line setting processing for setting a combining reference line on each of the measurement-object image and the comparison-object image; combining processing for combining the measurement-object image and the comparison-object image along the combining reference lines to form a combined image; and correction processing for correcting at least one of the measurement-object image and the comparison-object image so as to align their outlines on the combining reference line in the combined image when the outlines are not aligned.

The present invention affords an advantage in that it is possible to display a color of a measurement object, such as a vital tooth, and a color of a comparison object that is compared with the measurement object to a user in an easily comparable manner.

BRIEF DESCRIPTION OF THE SEVERAL VIEWS OF THE DRAWINGS

FIG. 7 is a diagram showing an example of a low-pass filter applied to an R signal and a B signal in a pixel-interpolation computation.

DETAILED DESCRIPTION OF THE INVENTION

An embodiment in the case where an image combining apparatus of the present invention is used in a dental colorimetry system will be described below with reference to the drawings.

Figure 1:
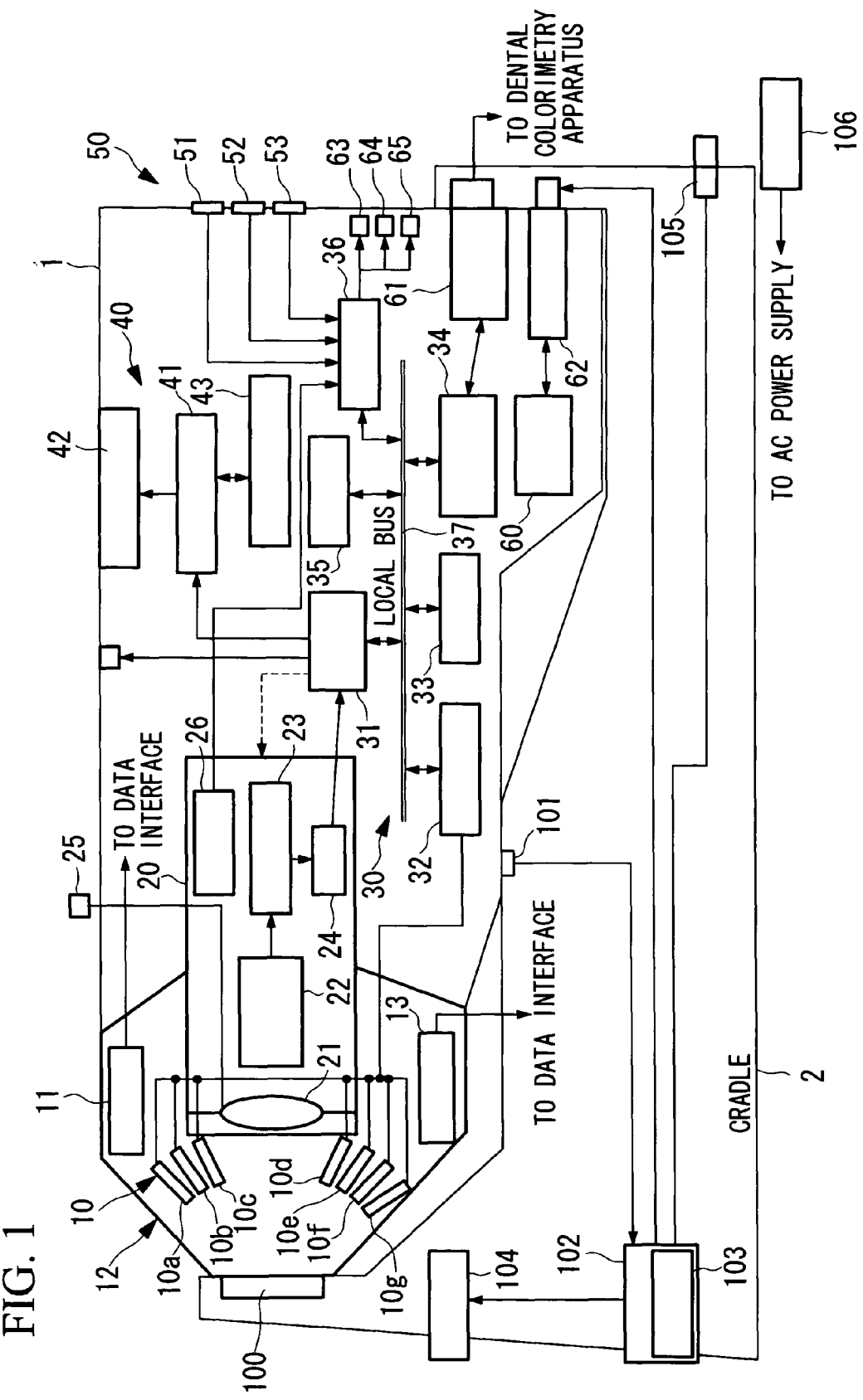
FIG. 1 is a block diagram showing, in outline, the configuration of an image-acquisition apparatus and a cradle according to an embodiment of the present invention.
Figure 4:
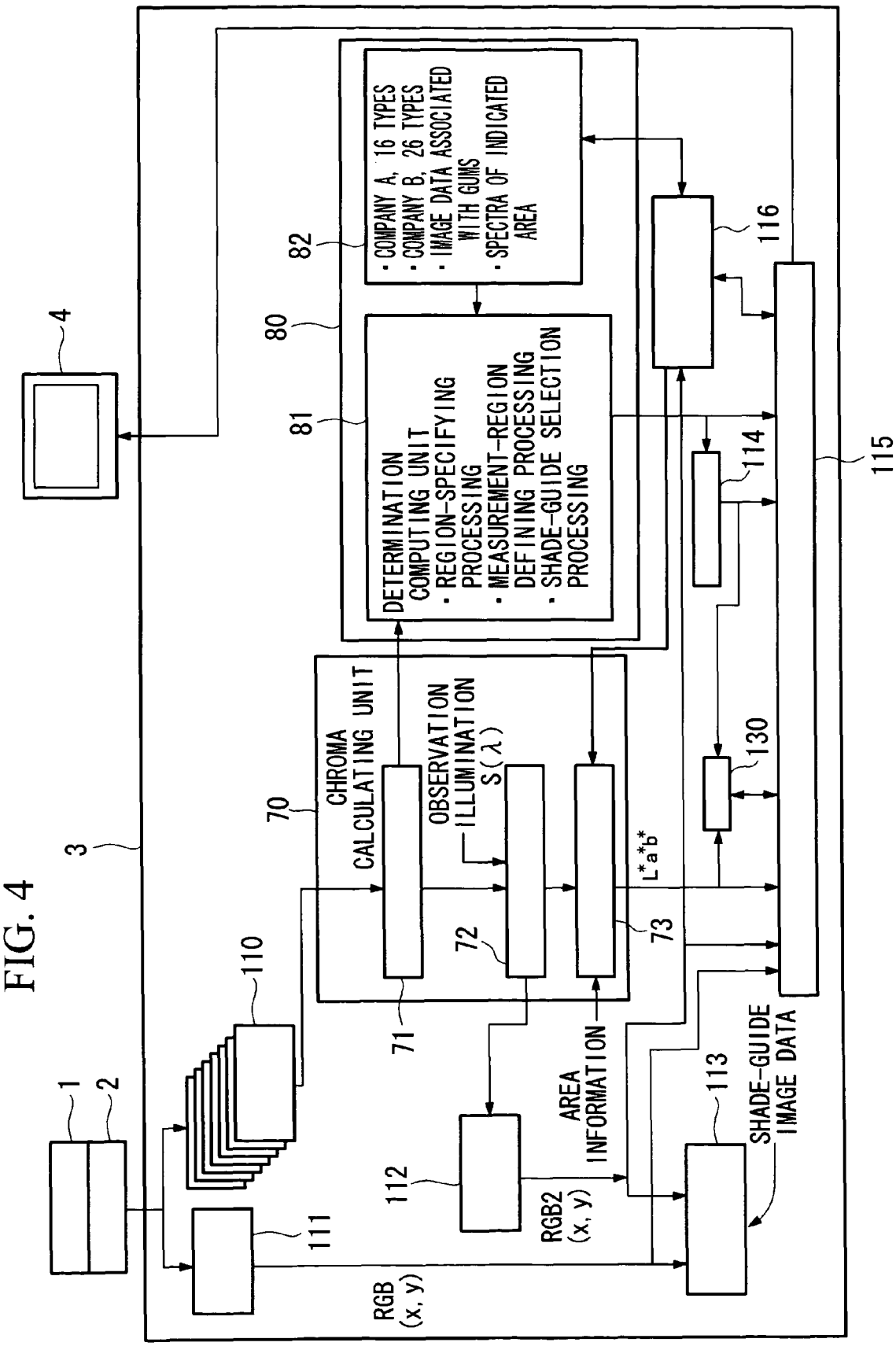
FIG. 4 is a block diagram showing, in outline, the configuration of a dental colorimetry apparatus according to the embodiment of the present invention.

As shown in FIGS. 1 and 4, a dental colorimetry system according to this embodiment includes an image-acquisition apparatus 1, a cradle 2, a dental colorimetry apparatus 3, and a display device 4.

As shown in FIG. 1, the image-acquisition apparatus 1 includes a light source 10, an image-acquisition unit 20, an image-acquisition control unit 30, a display unit 40, and an operating unit 50 as the main constituent elements thereof.

Figure 2:
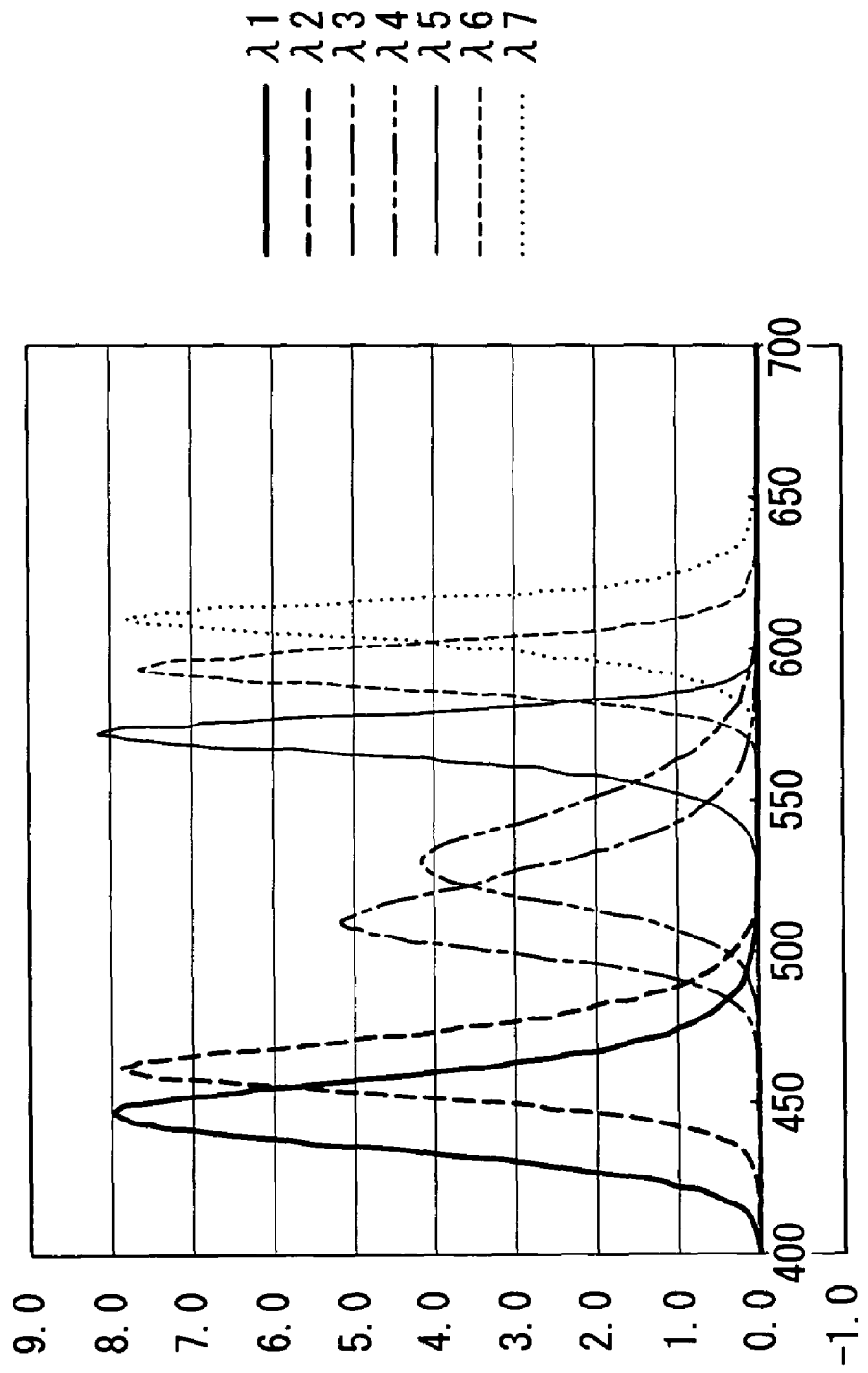
FIG. 2 is a graph showing the spectra of a light source illustrated in FIG. 1.

The light source 10 is disposed close to the tip of the image-acquisition apparatus 1 and emits illumination light having at least four different wavelength bands for illuminating an object. More specifically, the light source 10 is provided with seven light sources 10a to 10g which emit light in different wavelength bands. Each light source 10a to 10g includes four light emitting diodes (LEDs). As shown in FIG. 2, the central wavelengths thereof are as follows: the light source 10a, about 450 nm; the light source 10b, about 465 nm; the light source 10c, about 505 nm; the light source 10d, about 525 nm; the light source 10e, about 575 nm; the light source 10f, about 605 nm; and the light source 10g, about 630 nm. Emission-spectrum information about these LEDs is stored in an LED memory 11 and is used in the dental colorimetry apparatus 3, which is described later.

These light sources 10a to 10g are disposed, for example, in the form of a ring. Their arrangement is not particularly limited; for example, the four LEDs may be arranged in increasing order of wavelength, in reverse order, or randomly. In addition to all of the LEDs being disposed so as to form a single ring, they may be disposed so that the LEDs are divided into a plurality of groups and each group forms one ring. The configuration of the LEDs is not limited to the ring shape described above; it is possible to employ any configuration, such as a cross-shaped arrangement, a rectangular arrangement, or a random arrangement, so long as they do not obstruct image acquisition by the image-acquisition unit 20, which is described later. The light emitting elements of the light source 10 are not limited to LEDs; for example, it is possible to use another type of light emitting element or a semiconductor laser such as a laser diode (LD).

In the image-acquisition apparatus 1, an illumination optical system for radiating the illumination light from the light source 10 substantially uniformly over the surface of the object is provided at the object side of the light source 10. A temperature sensor 13 for detecting the temperature of the LEDs is provided in the vicinity of the light source 10.

The image-acquisition unit 20 includes an image-pickup lens 21, an RGB color image-acquisition device 22, a signal processor 23, and an analog-to-digital (A/D) converter 24. The image-pickup lens 21 forms an image of the object illuminated by the light source 10. The RGB color image-acquisition device 22 acquires an image of the object which is imaged by the image-pickup lens 21 and outputs an image signal. The RGB color image-acquisition device 22 is formed, for example, of a CCD, and the sensor responsivity thereof substantially covers a wide visible region of the spectrum. The CCD may be a monochrome or color device. The RGB color image-acquisition device 22 is not limited to a CCD; it is possible to use other types of devices, such as CMOS image sensors.

The signal processor 23 subjects the analog signal output from the RGB color image-acquisition device 22 to gain correction, offset correction, and so on. The A/D converter 24 converts the analog signal output from the signal processor 23 into a digital signal. A focus lever 25 for adjusting the focus is connected to the image-pickup lens 21. This focus lever 25 is used to manually adjust the focus, and a position detector 26 for detecting the position of the focus lever 25 is provided.

The image-acquisition control unit 30 includes a CPU 31, an LED driver 32, a data interface 33, a communication interface controller 34, an image memory 35, and an operating-unit interface 36. These components are each connected to a local bus 37 and are configured to enable transmission and reception of data via the local bus 37.

The CPU 31 controls the image-acquisition unit 20, records a spectral image of the object acquired and processed by the image-acquisition unit 20 in the image memory 35 via the local bus 37, and outputs the image to an LCD controller 41, which is described later. The LED driver 32 controls the light emission of each LED provided in the light source 10. The data interface 33 receives the contents of the LED memory 11 and information from the temperature sensor 13, which are provided at the light source 10. The communication interface controller 34 is connected to a communication interface contact point 61, which is used for external connection, and has a function for performing communication via a USB 2.0 connection, for example. The operating-unit interface 36 is connected to various operating buttons provided on the operating unit 50, which is described later, and functions as an interface for forwarding instructions input via the operating unit 50 to the CPU 31 via the local bus 37. The image memory 35 temporarily stores image data acquired in the image-acquisition unit 20. In this embodiment, the image memory 35 has sufficient capacity for storing at least seven spectral images and one RGB color image.

The display unit 40 includes the LCD controller 41 and a liquid crystal display (LCD) 42. The LCD controller 41 displays on the LCD 42 an image based on the image signal sent from the CPU 31, for example, the image currently being acquired by the image-acquisition unit 20 or a previously acquired image. As required, an image pattern stored in an overlay memory 43 may be superimposed on the image obtained from the CPU 31 and displayed on the LCD 42. The image pattern stored in the overlay memory 43 is, for example, a horizontal line for acquiring an image of the entire tooth horizontally, a cross line perpendicular thereto, an image-acquisition mode, an identification number of the acquired tooth, and so forth.

The operating unit 50 is provided with various operating switches and operating buttons for the user to input an instruction to commence spectral image acquisition and an instruction to commence or terminate moving-image acquisition. More specifically, the operating unit 50 includes an image-acquisition-mode switch 51, a shutter button 52, a viewer control button 53, and so forth. The image-acquisition-mode switch 51 is for switching between standard RGB image-acquisition and multispectral image acquisition. The viewer control button 53 is a switch for changing the image displayed on the LCD 42 and the like.

The image-acquisition apparatus 1 has a built-in lithium battery 60 serving as a storage battery. This lithium battery 60, which supplies electrical power to each component of the image-acquisition apparatus 1, is connected to a connection point 62 for charging. A battery LED 63 for indicating the charging status of this lithium battery is provided. In addition, a power LED 64 for indicating the status of the camera and an alarm buzzer 65 for indicating a warning during image acquisition are also provided in the image-acquisition apparatus 1.

The battery LED 63 is provided with three LEDs, for example, red, yellow, and green LEDs. The battery LED 63 indicates that the lithium battery 60 is sufficiently charged by glowing green; that the battery charge is low by glowing yellow, in other words, that charging is required; and that the battery charge is extremely low by glowing red, in other words, that charging is urgently required.

The power LED 64 is provided with two LEDs, for example, red and green LEDs. The power LED indicates that image-acquisition preparation has been completed by glowing green, that image-acquisition preparation is currently underway (initial warm-up and so on) by flashing green, and that the battery is currently being charged by glowing red.

The alarm buzzer 65 indicates that the acquired image data is invalid by issuing an alarm sound.

The cradle 2 supporting the image-acquisition apparatus 1 includes a color chart 100 for calibrating the image-acquisition unit 20; a microswitch 101 for determining whether or not the image-acquisition apparatus 1 is installed in the correct position; a power switch 102 for turning the power supply on and off; a power lamp 103 which turns on and off in conjunction with the on and off states of the power switch 102; and an installed lamp 104 for indicating whether or not the image-acquisition apparatus 1 is installed in the correct position by turning on and off in conjunction with the microswitch 101.

The installed lamp 104 glows green when, for example, the image-acquisition apparatus 1 is installed in the correct position and glows red when it is not installed. A power connector 105 is provided on the cradle 2, and an AC adaptor 106 is connected thereto. When the charge of the lithium battery 60 provided in the image-acquisition apparatus 1 is reduced and the battery LED 63 glows yellow or red, the cradle 2 is designed such that charging of the lithium battery starts when the image-acquisition apparatus 1 is placed in the cradle 2.

The image-acquisition apparatus 1 of the dental colorimetry system having such a configuration can perform both multispectral image acquisition and RGB image acquisition. In multispectral image acquisition, illumination light beams of seven wavelength bands (illumination light beams of seven primary colors) are sequentially radiated onto the object and seven spectral images of the object are acquired as still images. One RGB image-acquisition method is a method in which image acquisition of an object illuminated with natural light or room light, rather than illumination light of seven primary colors, is carried out using an RGB color CCD provided in the apparatus, just like a standard digital camera. By selecting one or more illumination beams from the illumination beams of seven primary colors as three RGB illumination beams and radiating them sequentially, it is also possible to acquire frame-sequential still images.

Among these image-acquisition modes, the RGB mode is used when acquiring an image of a large area, such as when acquiring a full-face image of a patient, a full-jaw image, and so on. On the other hand, multispectral image acquisition is used when accurately measuring the color of one or two of the patient's teeth, in other words, when performing colorimetry of the teeth.

Colorimetry processing of a tooth using multispectral image acquisition, which is the main subject matter of the present invention, will be described below.

Multispectral Image Acquisition

First, the image-acquisition apparatus is lifted from the cradle 2 by a dentist, and a contact cap is attached to a mounting hole (not shown in the drawings) provided at the side of the image-acquisition apparatus case from which light is emitted. This contact cap is made of a flexible material and has a substantially cylindrical shape.

Then, the image-acquisition mode is set to "colorimetry mode" by the dentist, whereupon the object is displayed as a moving image on the LCD 42. While looking at the image displayed on the LCD 42, the dentist positions the apparatus so that the vital tooth of the patient, which is the object to be measured, is disposed at a suitable position in the image-acquisition area and adjusts the focus using the focus lever 25. The contact cap is formed in a shape which guides the vital tooth to be measured to a suitable image-acquisition position, and therefore, it is possible to easily carry out this positioning.

Once positioning and focus adjustment have been completed, the dentist presses the shutter button 52, whereupon a signal to that effect is sent to the CPU 31 via the operating-unit interface 36, and multispectral image-acquisition is executed under the control of the CPU 31.

In multispectral image acquisition, by sequentially driving the light sources 10a to 10g with the LED driver 32, LED radiation light of different wavelength bands is sequentially radiated onto the object. The reflected light from the object forms an image on the surface of the RGB color image-acquisition device 22 in the image-acquisition unit 20, and is acquired as an RGB image. The acquired RGB image is sent to the signal processor 23. The signal processor 23 subjects the input RGB image signal to predetermined image processing and, from the RGB image signal, selects image data of one predetermined color in response to the wavelength bands of the light sources 10a to 10g. More specifically, the signal processor 23 selects the B image data from the image signal corresponding to the light sources 10a and 10b, selects the G image data from the image signal corresponding to the light sources 10c to 10e, and selects the R image data from the image signal corresponding to the light sources 10f and 10g. Therefore, the signal processor 23 selects image data of wavelengths which substantially match the central wavelengths of the illumination light.

The image data selected by the signal processor 23 is sent to the A/D converter 24 and is stored in the image memory 35 via the CPU 31. As a result, the color images selected from the RGB images corresponding to the central wavelengths of the LED are stored in the image memory 35 as multispectral images. During image acquisition, the LED radiation time and radiation intensity, the electronic shutter speed of the image-acquisition device, and so forth are controlled by the CPU 31 so that image acquisition of the respective wavelengths is performed with the proper exposure; if there is a severe temperature change during image acquisition, the alarm buzzer 65 emits an audible alarm.

Another image of the vital tooth is acquired without illuminating the LEDs and is stored in the image memory 35 as an external-light image.

Next, once image acquisition has been completed and the image-acquisition apparatus 1 is placed in the cradle 2 by the dentist, calibration image measurement performed.

The calibration image measurement is for acquiring an image of the color chart 100 using the same procedure as that used for the multispectral image acquisition described above. Accordingly, a multispectral image of the color chart 100 is stored in the image memory 35 as a color-chart image.

Next, image acquisition of the color chart 100 is carried out without illuminating any of the LEDs (under darkness), and this image is stored in the image memory 35 as a dark-current image. This dark-current image may be formed by performing image acquisition a plurality of times and averaging the images obtained.

Next, signal correction using the above-described external-light image and dark-current image stored in the image memory 35 is performed for the multispectral image and the color-chart image, respectively. The signal correction for the multispectral image is performed, for example, by subtracting a signal value of the external-light image data at each pixel from the image data of the multispectral image, which allows the effect of external light during image acquisition to be eliminated. Similarly, the signal correction for the color-chart image is carried out, for example, by subtracting a signal value of the dark-current image data at each pixel from the image data of the color-chart image, which allows dark-current noise of the CCD, which changes depending on temperature, to be removed.

Figure 3:
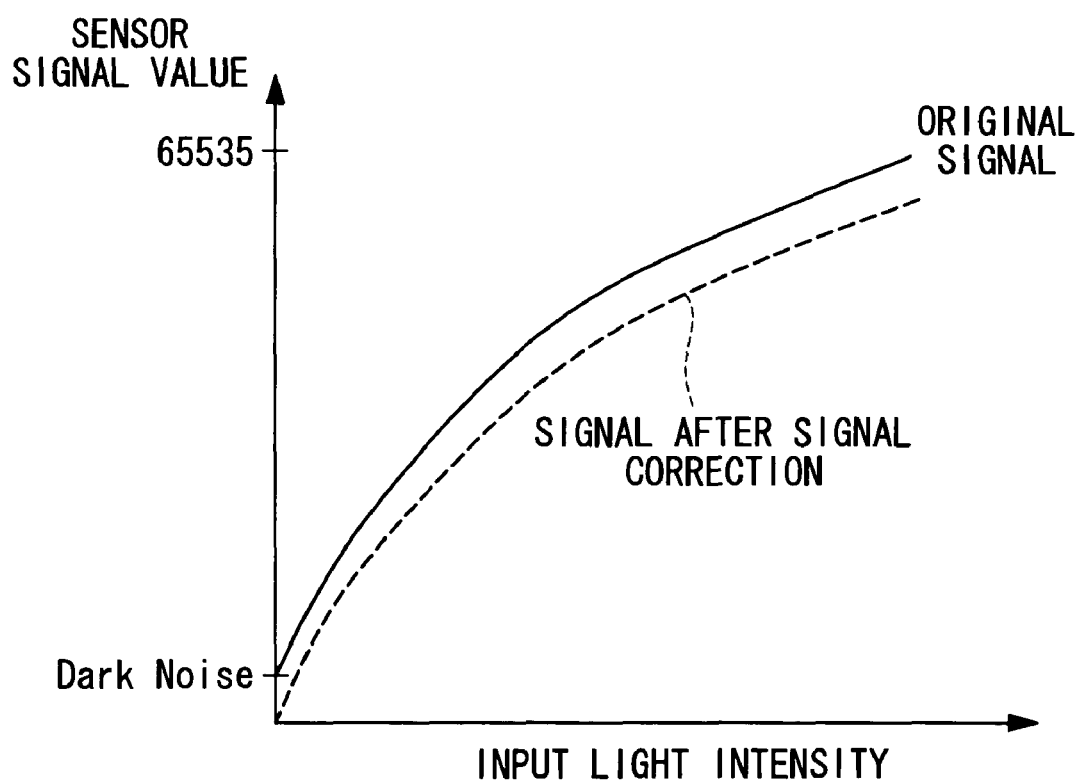
FIG. 3 is a graph for explaining signal correction.

FIG. 3 shows an example of the signal correction results for the color-chart image. In FIG. 3, the vertical axis indicates the sensor signal value and the horizontal axis indicates the input light intensity. The solid line shows the original signal before correction and the dotted line shows the signal after correction.

After signal correction, the multispectral image and the color-chart image are sent to the dental colorimetry apparatus 3 via the local bus 37, the communication interface controller 34, and the communication interface connection point 61 and are stored in a multispectral image memory 110 in the dental colorimetry apparatus 3, as shown in FIG. 4.

The system may also be configured such that the multispectral image and dark-current image of the above-described color chart 100 are sent directly to the dental colorimetry apparatus 3 via the local bus 37, the communication interface controller 34, and the communication interface connection point 61, without being stored in the image memory 35 in the image-acquisition apparatus 1, and are stored in the multispectral image memory 110 in the dental colorimetry apparatus 3. In such a case, the signal correction described above is carried out in the dental colorimetry apparatus 3.

The dental colorimetry apparatus 3, which is formed, for example, of a personal computer, receives the multispectral image and the color-chart image output via the communication interface connection point 61 in the image-acquisition apparatus 1, and subjects the multispectral image to various types of processing. By doing so, it forms an image of the tooth (the object) which has a high degree of color reproducibility, selects an appropriate shade-guide number for the tooth, and displays this information on the display device 4.

As shown in FIG. 4, for example, the dental colorimetry apparatus 3 includes a chroma calculating unit 70, a shade-guide-number determining unit 80, the multispectral image memory 110, an RGB image memory 111, a color-image-generating processor 112, an image filing unit 113, a shade-guide chroma-data storage unit 114, an image-display GUI unit (display control unit) 115, an image combining unit (image combining device) 116, and a difference calculating unit 130.

The chroma calculating unit 70 includes a spectrum-estimation computing unit 71, an observation-spectrum computing unit 72, and a chroma-value computing unit 73. The shade-guide-number determining unit 80 includes a determination computing unit 81 and a shade-guide reference-imagedata storage unit 82. This shade-guide reference-image-data storage unit 82 stores, for example, shade-guide image data, in association with shade guide numbers, for each manufacturer producing shade guides in which color samples are arranged in rows; in addition, it also stores spectral reflectance curves for predetermined areas of these shade guides and shade guide images associated with the gums.

In the dental colorimetry apparatus 3 having such a configuration, the multispectral image and color-chart image sent from the image-acquisition apparatus 1 are first stored in the multispectral-image memory 110, and thereafter are sent to the chroma calculating unit 70. In the chroma calculating unit 70, first, spectrum (in this embodiment, a spectral reflectance curve) estimation processing and so forth are carried out by the spectrum-estimation computing unit 71.

Figure 5:
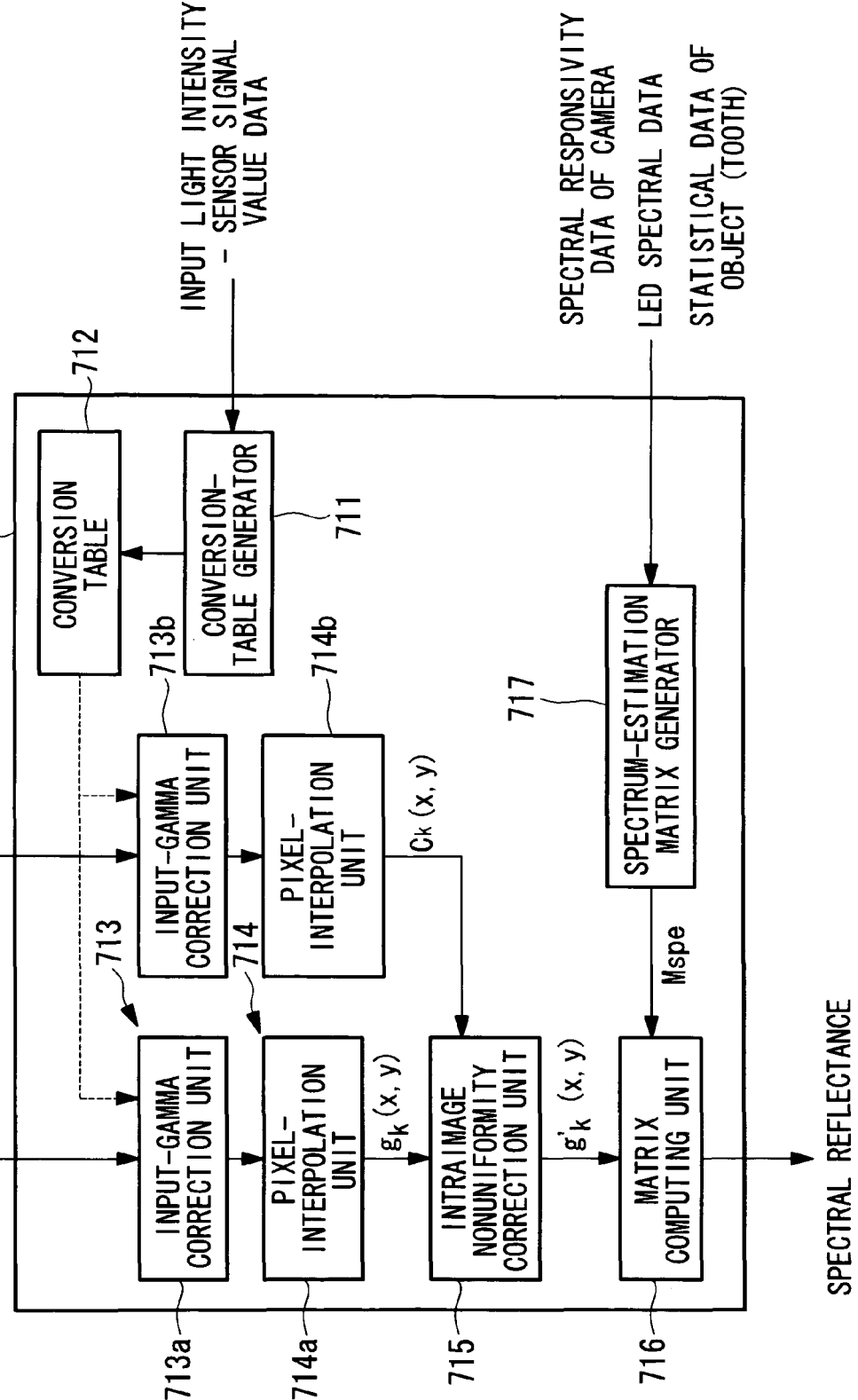
FIG. 5 is a schematic diagram of the internal configuration of a spectrum-estimation computing unit illustrated in FIG. 4.

As shown in FIG. 5, the spectrum-estimation computing unit 71 includes a conversion-table generator 711, a conversion table 712, an input-gamma correction unit 713, a pixel-interpolation unit 714, an intraimage nonuniformity correction unit 715, a matrix computing unit 716, and a spectrum-estimation matrix generator 717. Separate input-gamma correction units 713 and pixel-interpolation units 714 are provided for the multispectral image and the color-chart image, respectively; that is, an input-gamma correction unit 713a and a pixel-interpolation unit 714a are provided for the multispectral image, and an input-gamma correction unit 713b and a pixel-interpolation unit 714b are provided for the color-chart image.

In the spectrum-estimation computing unit 71 having such a configuration, first the multispectral image and the color-chart image are sent to the separate input-gamma correction units 713a and 713b, respectively, and after input-gamma correction is performed, they are subjected to pixel-interpolation processing by the corresponding pixel-interpolation units 714a and 714b. The signals obtained after this processing are sent to the intraimage nonuniformity correction unit 715, where intraimage nonuniformity correction processing is performed on the multispectral image using the color-chart image. Thereafter, the multispectral image is sent to the matrix computing unit 716, and the spectral reflectance is calculated using a matrix generated by the spectrum-estimation matrix generator 717.

The image processing carried out in each unit will be described more concretely below.

Figure 6A:
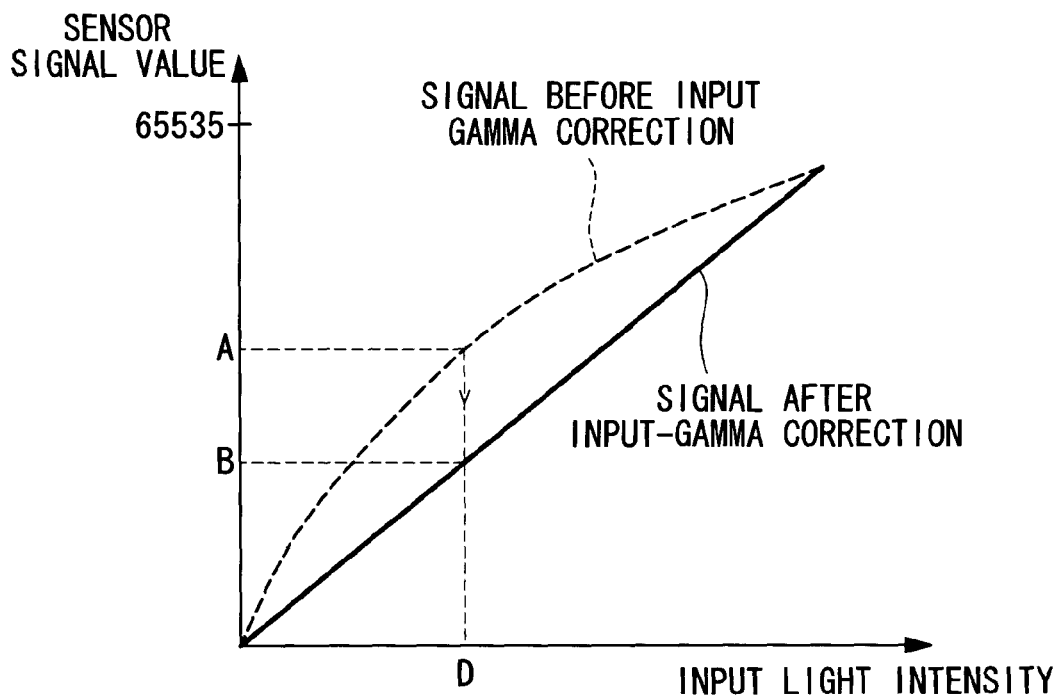
FIGS. 6A and 6B are graphs for explaining input gamma correction.

First, prior to input-gamma correction, the conversion table 712 is created by the conversion-table generator 711. More specifically, the conversion-table generator 711 contains data associating the input light intensity and the sensor signal value, and it creates the conversion table 712 based on this data. The conversion table 712 is created from the relationship between the input light intensity and the output signal value; as shown by the solid line in FIG. 6A for example, it is created such that the input light intensity and the sensor signal value are substantially linearly proportional.

Figure 6B:
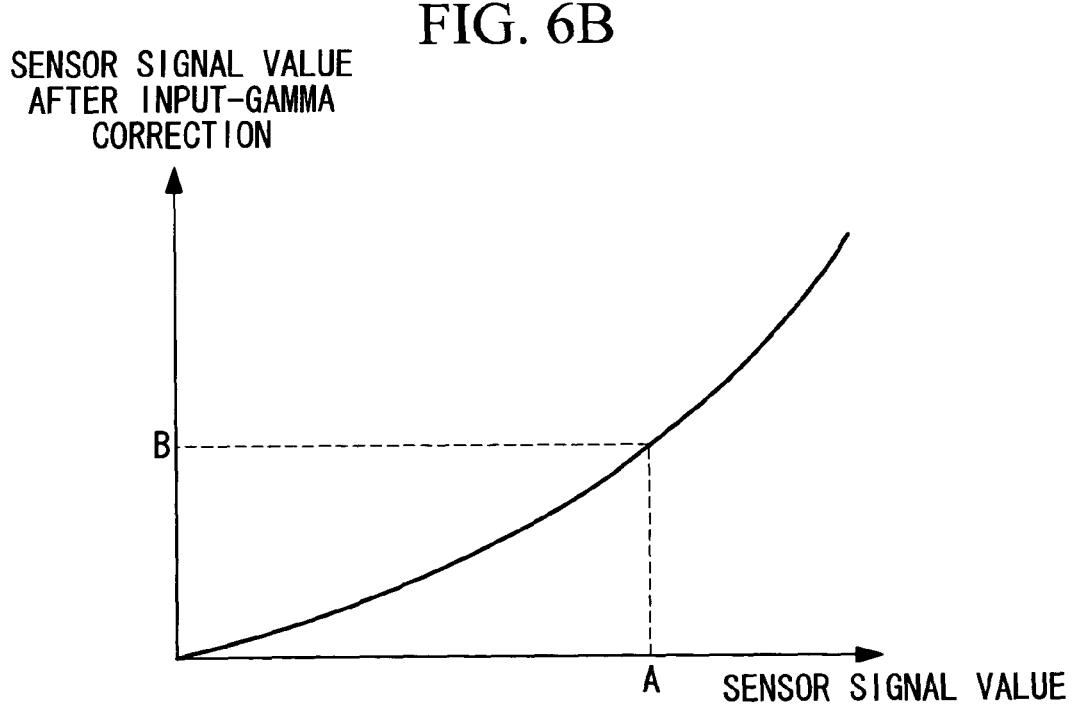

The input-gamma correction units 713a and 713b perform input-gamma correction on the multispectral image and the color-chart image, respectively, by referring to this conversion table 712. This conversion table 712 is created such that an input light intensity D corresponding to a current sensor value A is obtained and an output sensor value B corresponding to this input light intensity D is output; the result is shown in FIG. 6B. Accordingly, when input-gamma correction is performed on the multispectral image and the color-chart image, the corrected image data is sent to the pixel-interpolation units 714a and 714b, respectively.

Figure 7:
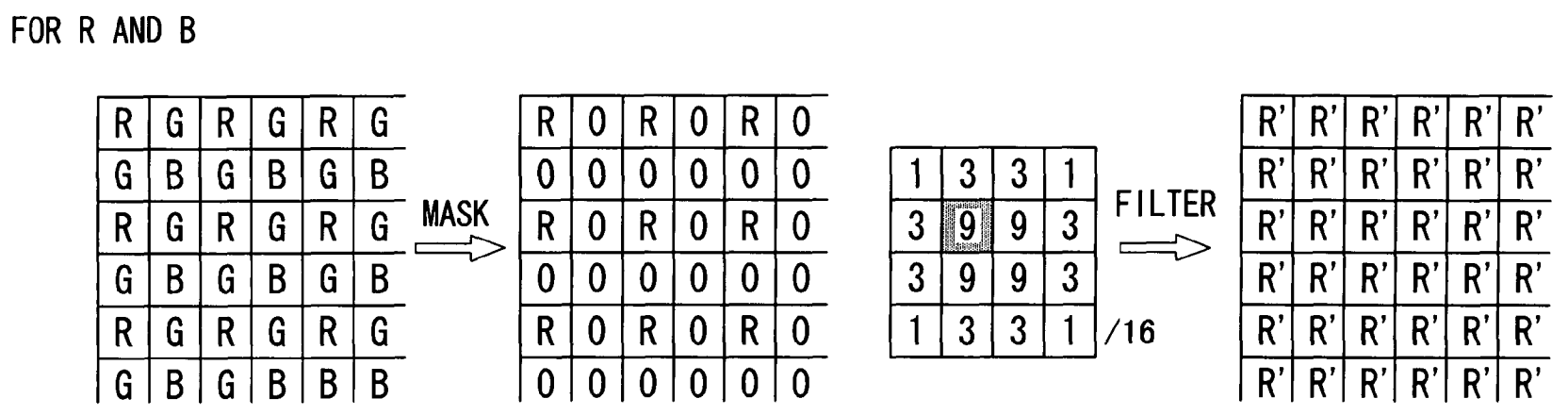
Figure 8:
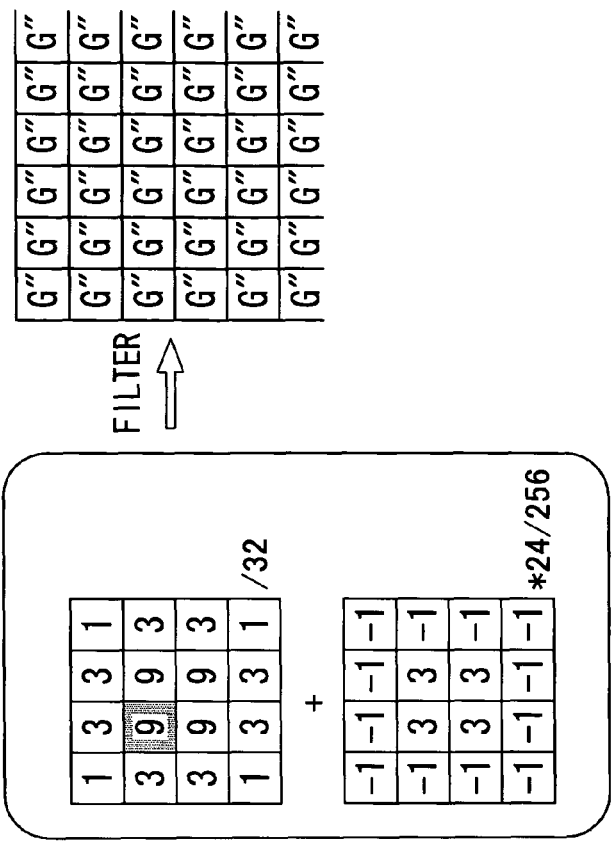
FIG. 8 is a diagram showing an example of a low-pass filter applied to a G signal in the pixel-interpolation computation.

In the pixel-interpolation units 714a and 714b, pixel interpolation is performed by multiplying each of the multispectral image data and the color-chart image data, which have been subjected to input-gamma correction, by a low-pass filter for pixel interpolation. FIG. 7 shows an example of a low-pass filter applied to the R signal and the B signal. FIG. 8 shows a low-pass filter applied to the G signal. By multiplying each multispectral image data value by such low-pass filters for pixel interpolation, a 144×144 pixel image, for example, becomes a 288×288 pixel image.

Image data $g_k(x, y)$ which has been subjected to image interpolation is then sent to the intraimage nonuniformity correction unit 715.

The intraimage nonuniformity correction unit 715 corrects the luminance at the center of the screen of the multispectral image data using equation (1) below.

$$g'_k(x, y) = g_k(x, y) \frac{\sum_{\eta=y_0-\delta/2}^{y_0+\delta/2} \sum_{\xi=x_0-\delta/2}^{x_0+\delta/2} c_k(\xi, \eta)/\delta^2}{\sum_{\eta=y-\delta/2}^{y+\delta/2} \sum_{\xi=x-\delta/2}^{x+\delta/2} c_k(\xi, \eta)/\delta^2} \quad (1)$$

In equation (1), $c_k(x, y)$ is acquired image data of the color chart, $g_k(x, y)$ is the multispectral image data after input-gamma correction, $(x_0, y_0)$ is the center pixel position, $\delta(=5)$ is the area averaging size, and $g'_k(x, y)$ is the image data after intraimage nonuniformity correction (where $k=1, \ldots, N$ (the number of wavelength bands)).

The intraimage nonuniformity correction described above is performed on each data value of the multispectral image data.

The multispectral image data after intraimage nonuniformity correction, $g'_k(x, y)$, is sent to the matrix computing unit 716. The matrix computing unit 716 performs spectrum (spectral reflectance) estimation processing using the multispectral image data $g'_k(x, y)$ from the intraimage nonuniformity correction unit 715. In this spectrum (spectral reflectance) estimation processing, in the wavelength band from 380 nm to 780 nm, estimation of the spectral reflectance is performed in 1-nm intervals. That is, in this embodiment, 401-dimension spectral reflectance data is estimated.

Generally, in order to obtain spectral reflectances for each single wavelength, large, expensive spectrometers or the like are used. In this embodiment, however, because the subjects are limited to teeth, by using predetermined characteristics of those objects, the 401-dimensional spectral reflectance data can be estimated with a small number of bands.

More specifically, the 401-dimensional spectral signal is calculated by performing a matrix calculation using the multispectral image data $g'_k(x, y)$ and a spectrum-estimation matrix Mspe.

The spectrum-estimation matrix Mspe described above is created in the spectrum-estimation matrix generator 717 based on spectral responsivity data of the camera, spectral data of the LEDs, and statistical data of the object (tooth). The creation of this spectrum-estimation matrix is not particularly limited; known methods in the literature may be used. One example is described in detail in S. K. Park and F. O. Huck, "Estimation of spectral reflectance curves from multispectrum image data", Applied Optics, Vol. 16, pp. 3107-3114 (1977).

The spectral responsivity data of the camera, the spectral data of the LEDs, the statistical data of the object (tooth), and so on are stored in advance in the image filing unit 113 shown in FIG. 4. If the spectral responsivity of the camera changes depending on the sensor position, position-dependent spectral responsivity data may be obtained, or appropriate correction may be performed on the data for the central position.

When the spectral reflectance is computed by the spectrum-estimation computing unit 71, the computation result is sent, together with the multispectral image data, to the shade-guide-number determining unit 80 and the observation-spectrum computing unit 72 in the chroma calculating unit 70, as shown in FIG. 4.

Information from the spectrum-estimation computing unit 71 is sent to the determination computing unit 81 in the shade-guide-number determining unit 80. In the determination computing unit 81, first, region-specifying processing for specifying a tooth region to be measured is carried out.

Here, information about the vital tooth to be measured, as well as information about the neighboring teeth, the gum, and so forth, is also included in the multispectral image data acquired by the image-acquisition apparatus 1. Therefore, processing for specifying the vital tooth region to be measured from this oral-cavity image data is carried out in the region-specifying processing.

Figure 9:
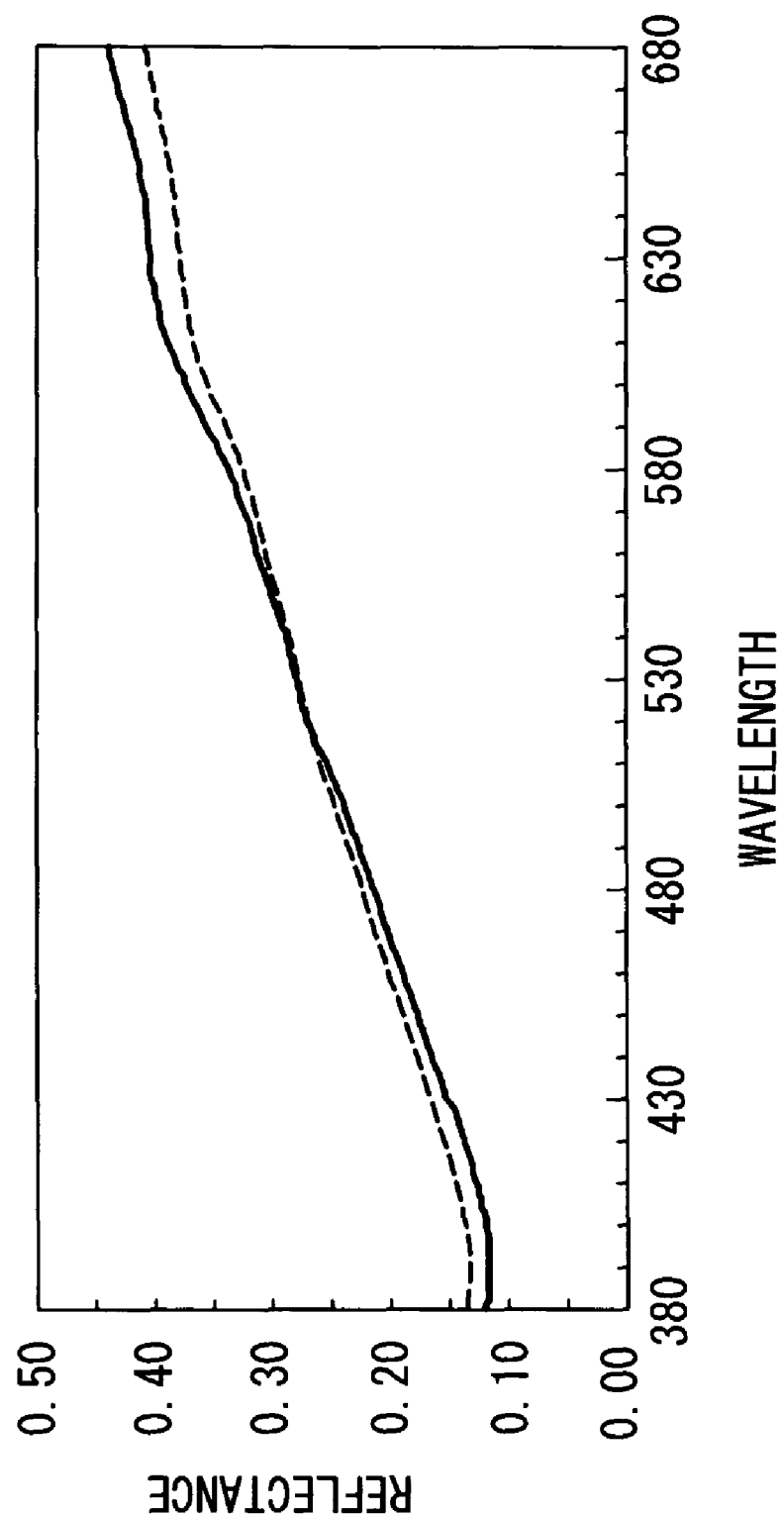
FIG. 9 is a graph showing an example of a reflectance spectrum of a vital tooth (number of samples, n=2).
Figure 10:
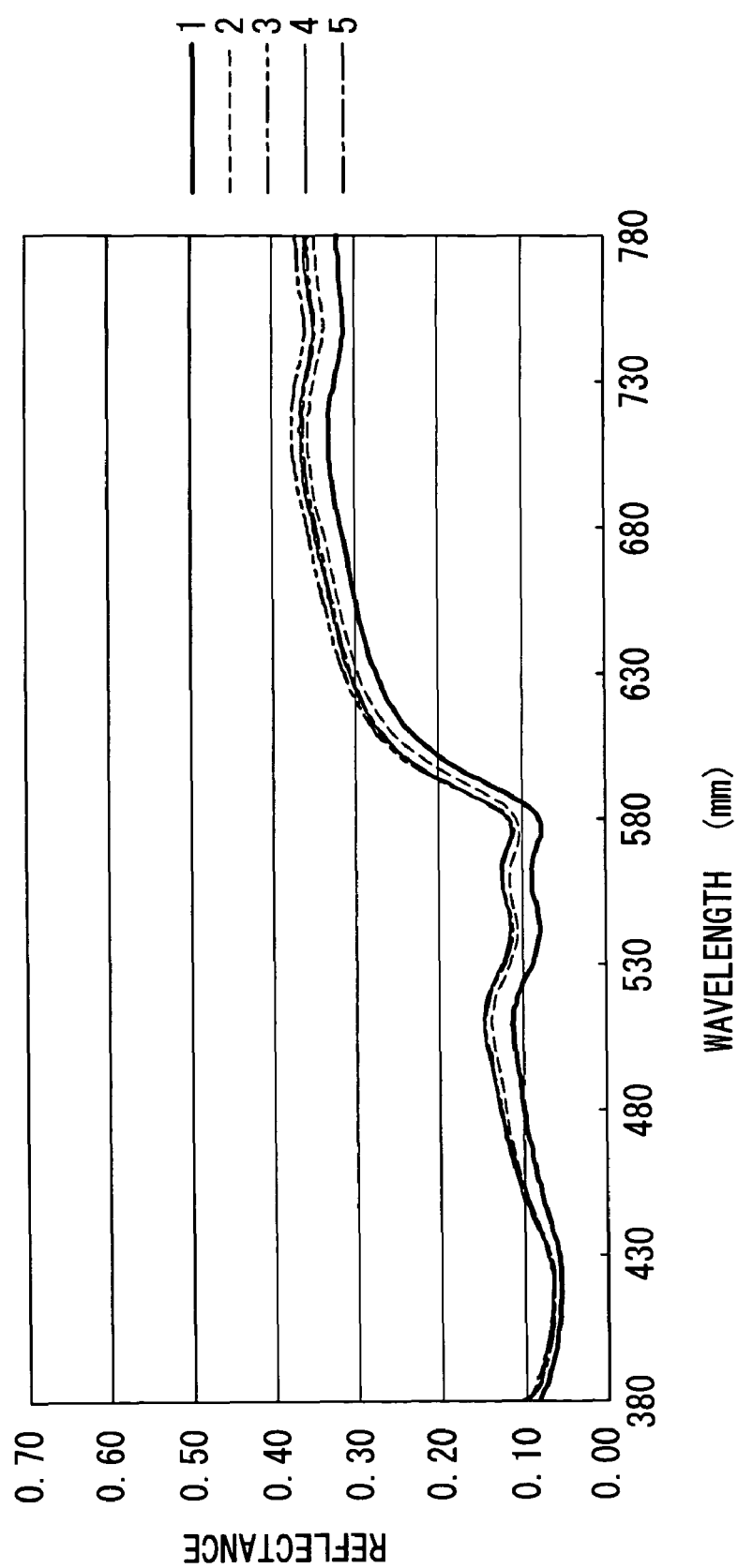
FIG. 10 is a graph showing an example of the reflectance spectrum of gums (number of samples, n=5).

An example of the reflectance spectrum of the tooth (number of samples, n=2) is shown in FIG. 9, and an example of the reflectance spectrum of the gum (number of samples, n=5) is shown in FIG. 10. In FIGS. 9 and 10, the horizontal axis indicates wavelength and the vertical axis indicates reflectance. Because the tooth is completely white and the gum is red, there is a large difference between the two spectra in the blue wavelength band (for example, from 400 nm to 450 nm) and in the green wavelength band (for example, from 530 nm to 580 nm), as is clear from FIGS. 9 and 10. Thus, in this embodiment, noting that the vital tooth has a specific reflectance spectrum, the vital tooth region is specified by extracting from the image data pixels exhibiting this specific vital tooth reflectance spectrum.

Vital-Tooth-Region Specifying Method 1

In this method, in a region in the image represented by the acquired multispectral image data (a pixel or a group of pixels), wavelength-band characteristic values determined by respective signal values of n wavelength bands form an n-dimensional space. Thus, in this dimensional space, a plane representing the characteristic of the measured object is defined. When the wavelength-band characteristic values represented in the n-dimensional space are projected onto this plane, the region (outline) to be measured is specified by determining that the region in the image having that wavelength-band characteristic value is included in the vital tooth region to be measured.

Figure 11:
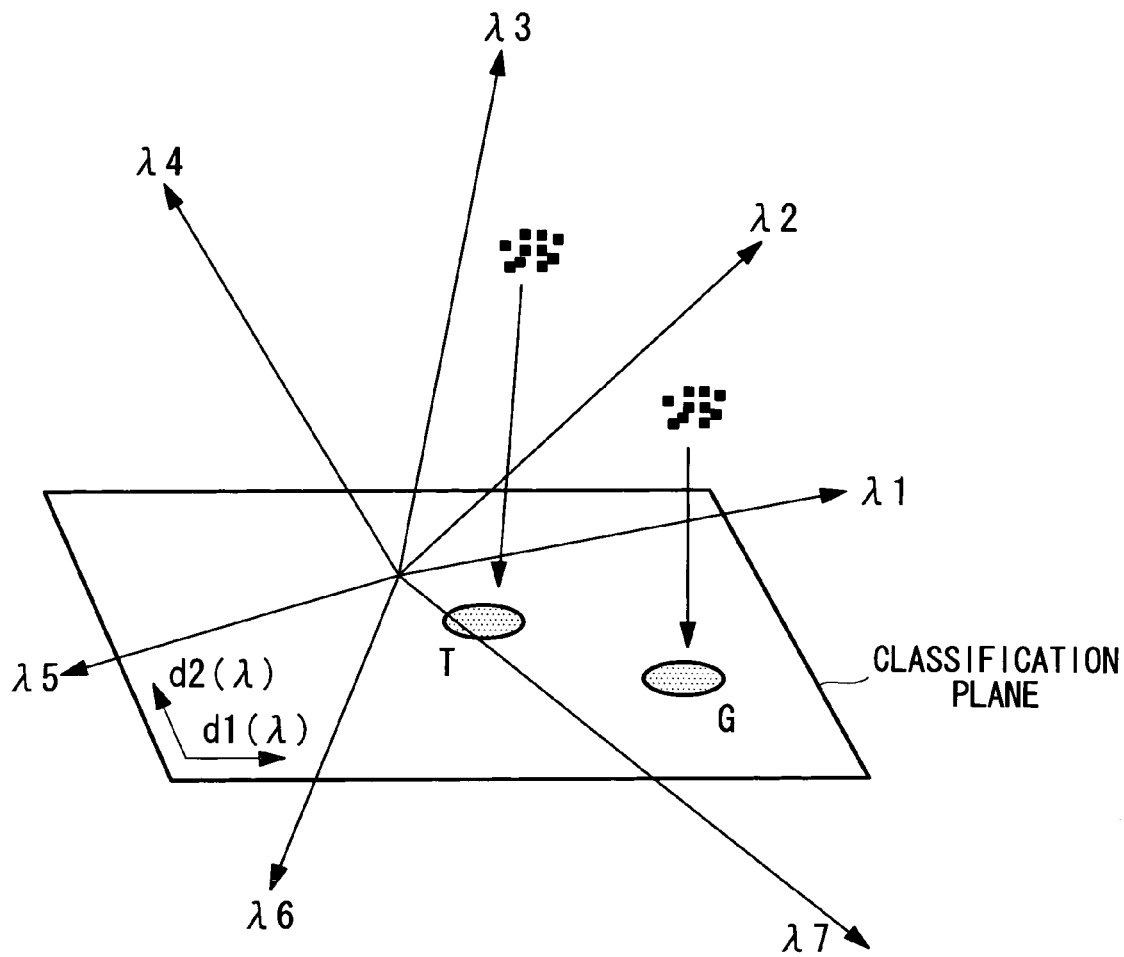
FIG. 11 is a diagram for explaining a method of specifying a vital tooth region according to the embodiment of the present invention.

FIG. 11 illustrates the method for specifying the vital tooth region to be measured using this method. As shown in FIG. 11, a 7-dimensional space is formed by seven wavelengths $\lambda 1$ to $\lambda 7$. A classification plane for optimally separating the vital tooth to be measured is defined in the 7-dimensional space. More specifically, classification spectra $d1(\lambda)$ and $d2(\lambda)$ for plane projection are determined. Then, a predetermined region is first cut out from the acquired multispectral image data, and a feature value which is represented in the 7-dimensional space is computed as the wavelength-band characteristic value. The feature value is a combination of seven signal values obtained when each band in the cut-out region is averaged in this region and converted to seven signal values. The size of the cut-out region is, for example 2 pixels×2 pixels, but it is not limited to this size; it may be 1 pixel×1 pixel, or it may be 3 pixels×3 pixels or larger.

The feature value is represented by a single point in the 7-dimensional space in FIG. 11. The single point in the 7-dimensional space represented by this feature value is projected onto the classification plane to obtain one point on the classification plane. The coordinates of the point on the classification plane can be obtained from the inner product of the classification spectra $d1(\lambda)$ and $d2(\lambda)$. If the point on the classification plane is included in a region T on the classification plane, determined by the characteristic spectrum of the vital tooth, that is, in a planar region representing the characteristics of the measured object, the cut-out region is determined to be included within the outline of the vital tooth. On the other hand, if the point on the classification plane is included in a region G, determined by the characteristic spectrum of the gum, the cut-out region is determined to be included within the outline of the gum.

In this method, the vital tooth region is specified by sequentially carrying out this determination while changing the cut-out region. In particular, the vital tooth region to be measured is normally positioned close to the center of the image represented by the acquired multispectral image data. Therefore, the vital tooth region to be measured (in other words, the outline of the vital tooth to be measured) is specified by sequentially carrying out the above-described determination of whether or not the cut-out region is included in the vital tooth region while moving the cut-out region from the vicinity of the center of the image towards the periphery. In particular, this embodiment is advantageous in that it is possible more accurately specify the region (outline) to be measured, because the feature value is defined in a 7-dimensional space, which has more dimensions than a 3-dimensional space formed by the standard RGB image.

Vital-Tooth-Region Specifying Method 2

In addition to the region specifying method based on the classification spectrum described above, this method specifies as the vital tooth region a region having a signal value (spectrum) that is unique to the vital tooth. This is achieved by extracting, for example, only signal values (spectra) corresponding to the blue wavelength band and the green wavelength band and comparing these signal values. According to this method, because the number of samples to compare is low, it is possible to easily carry out region specifying in a short period of time.

More concretely, similar to the case described above where region specifying is carried out based on the classification spectrum, by detecting the position of an inflection point where the spectral characteristic value changes suddenly while moving the position from the vicinity of the center of the image towards the periphery, that position is determined to be the outline of the vital tooth to be measured. For example, an object to be detected (vital tooth) and an object to be separated (an object other than the vital tooth, such as the gum) are compared, characteristic bands $\lambda 1$ and $\lambda 2$ are selected, and the ratio thereof yields the spectral characteristic value. When the object to be detected is a vital tooth, the ratio of two points is calculated as, for example, $\lambda 1=450$ nm and $\lambda 2=550$ nm to obtain the inflexion point of that ratio. Accordingly, it is possible to determine the boundary with the neighboring vital tooth and to obtain pixels of the vital tooth to be measured. In addition to performing specifying for each pixel, it is also possible to take the average of pixel groups including a plurality of pixels and to perform specifying for each pixel group based on this average.

Whichever of the vital-tooth-region specifying methods 1 and 2 described above is used, in this embodiment, region specification is carried out for the vital tooth. However, it is also possible to carry out region specification for the gum. Apart from vital teeth, it can also be used in other applications, for example, region specification of blemishes, freckles, and so forth in dermatology, region specification of a predetermined paint color within a multicolor painted pattern, and so on. In these cases, a specific spectrum of the region to be specified, such as the gum, blemish, freckle, paint etc., may be used. For example, when performing region specification of a blemish or freckle, a specific spectrum of a benign blemish or freckle and a specific spectrum of a malignant blemish or freckle are stored in advance, and by specifying regions close to these spectra, it is possible to easily perform region specification of the measurement object.

Figure 12:
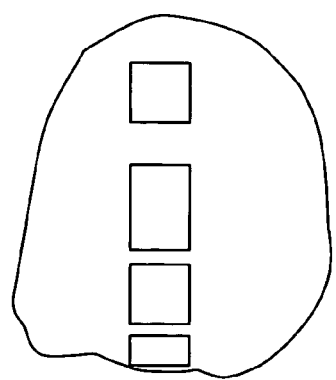
FIG. 12 is a diagram showing an example of measurement regions defined in a measurement-region defining processing.

Accordingly, once the pixels of the vital tooth to be measured are specified, next, measurement-region defining processing is carried out for defining measurement regions in the vital tooth region to be measured. As shown in FIG. 12, these measurement regions are defined as rectangular regions at the top, middle, and bottom of the tooth surface. For example, regions having areas with fixed ratios with respect to their height on the vital tooth are defined. In other words, whether the vital tooth is large or small, the measurement regions and the positions thereof are defined with a constant ratio. The shapes of the measurement regions are not limited to the rectangular shapes shown in FIG. 12; for example, the shapes may be circular, elliptical, or asymmetric.

Next, shade-guide selection processing (sample selection processing) for selecting the closest shade guide is carried out for each measurement region defined as described above. In this shade-guide selection processing, the color of the vital tooth to be measured and the color of the shade guide are compared to determine whether they match. This comparison is carried out for each measurement region defined as described above; it is performed by comparing the spectrum (in this embodiment, the spectral reflectance) of the measurement region and the spectrum (in this embodiment, the spectral reflectance) of each shade guide stored in advance in the shade-guide reference-image data storage unit 82 to determine the shade guide having the minimum difference between the two spectra.

This is achieved, for example, by obtaining a spectrum-determining value (J value) based on equation (2) below.

$$Jvalue = C\sqrt{\frac{\sum_\lambda ((f_1(\lambda) - f_2(\lambda))^2 E(\lambda)^2)}{n}} \quad (2)$$

In equation (2), J value is the spectrum-determining value, C is a normalization coefficient, n is the sample number (number of wavelengths used in the calculation), $\lambda$ is wavelength, $f_1(\lambda)$ is the spectral responsivity curve of the vital tooth to be determined, $f_2(\lambda)$ is the spectral responsivity curve of the shade guide, and $E(\lambda)$ is a determination responsivity correction curve. In this embodiment, weighting related to the spectral responsivity, which depends on the wavelength $\lambda$, is performed using $E(\lambda)$.

Accordingly, the spectral curves of shade guides of each company are substituted for $f_2(\lambda)$ in equation (2) above to calculate the respective spectrum-determining values, J value. The shade guide exhibiting the smallest spectrum-determining value, J value, is determined to be the shade-guide number closest to the tooth. In this embodiment, a plurality of candidates (for example, three) are extracted in order of smallest spectrum-determining value, J value. Of course, it is also possible for the number of candidates to be extracted to be one. The determination responsivity correction curve $E(\lambda)$ in equation (2) above may have various weights.

When the shade-guide number is selected in this way, the number is sent from the determination computing unit 81 to the shade-guide chroma-data storage unit 114 and the image-display GUI unit 115. Chroma data corresponding to the selected shade-guide number is then sent from the shade-guide chroma-data storage unit 114 to the image-display GUI unit 115 and the difference calculating unit 130. The spectrum-determining value (J value) for each shade-guide number is sent from the determination computing unit 81 to the image-display GUI unit 115.

On the other hand, in the observation-spectrum computing unit 72 of the chroma calculating unit 70, a spectrum G(x, y, $\lambda$) of the object under the illumination light used for observation is obtained by multiplying the illumination light spectrum S($\lambda$) used for observation by the spectrum of the vital tooth obtained in the spectrum-estimation computing unit 71. S($\lambda$) is the spectrum of the light source used for observing the color of the vital tooth, such as a D65 or D55 light source, a fluorescent light source, or the like. This data is stored in advance in an input-profile storage unit (not shown). The spectrum of the object under the illumination light used for observation, which is obtained in the observation-spectrum computing unit 72, is sent to the chroma-value computing unit 73 and the color-image-generating processor 112.

In the chroma-value computing unit 73, L*a*b* chromaticity values are calculated for each pixel from the spectrum of the object under the illumination light used for observation, and averages of the L*a*b* chromaticity values in predetermined areas are calculated and sent to both the image-display GUI unit 115 and the difference calculating unit 130. These predetermined areas are defined, for example, at three positions at the top, middle, and bottom of the vital tooth.

On the other hand, the spectrum G(x, y, $\lambda$) of the object under the illumination light used for observation is sent from the observation-spectrum computing unit 72 to the color-image-generating processor 112, and RGB2(x, y), which is an RGB image for displaying on the monitor, is created and sent to the image-display GUI unit 115. This RGB image may be subjected to edge enhancement and so forth.

The difference calculating unit 130 calculates differences $\Delta E$, $\Delta L^*$, $\Delta a^*$, and $\Delta b^*$ between the chromaticity values of the tooth and the chromaticity values of the shade guide on the basis of the averages of the L*a*b* chromaticity values in the predetermined areas sent from the chroma-value computing unit 73 and the chroma data sent from the shade-guide chroma-data storage unit 114. The difference calculating unit 130 also calculates differences $\Delta E$, $\Delta L^*$, $\Delta a^*$, and $\Delta b^*$ between the chromaticity values of the tooth and the chromaticity values of the shade guide for each pixel on the basis of a predetermined position of the tooth. Here, an example of the "predetermined position" is, as described below, the intersection of a vertical scanning line Y and a horizontal scanning line X that are displayed on each of a tooth image and a shade guide image. The differences $\Delta E$, $\Delta L^*$, $\Delta a^*$, and $\Delta b^*$ in chromaticity values between the tooth and the shade guide in the predetermined areas and the differences $\Delta E$, $\Delta L^*$, $\Delta a^*$, and $\Delta b^*$ in chromaticity values calculated for each pixel are sent to the image-display GUI unit 115.

Figure 13:
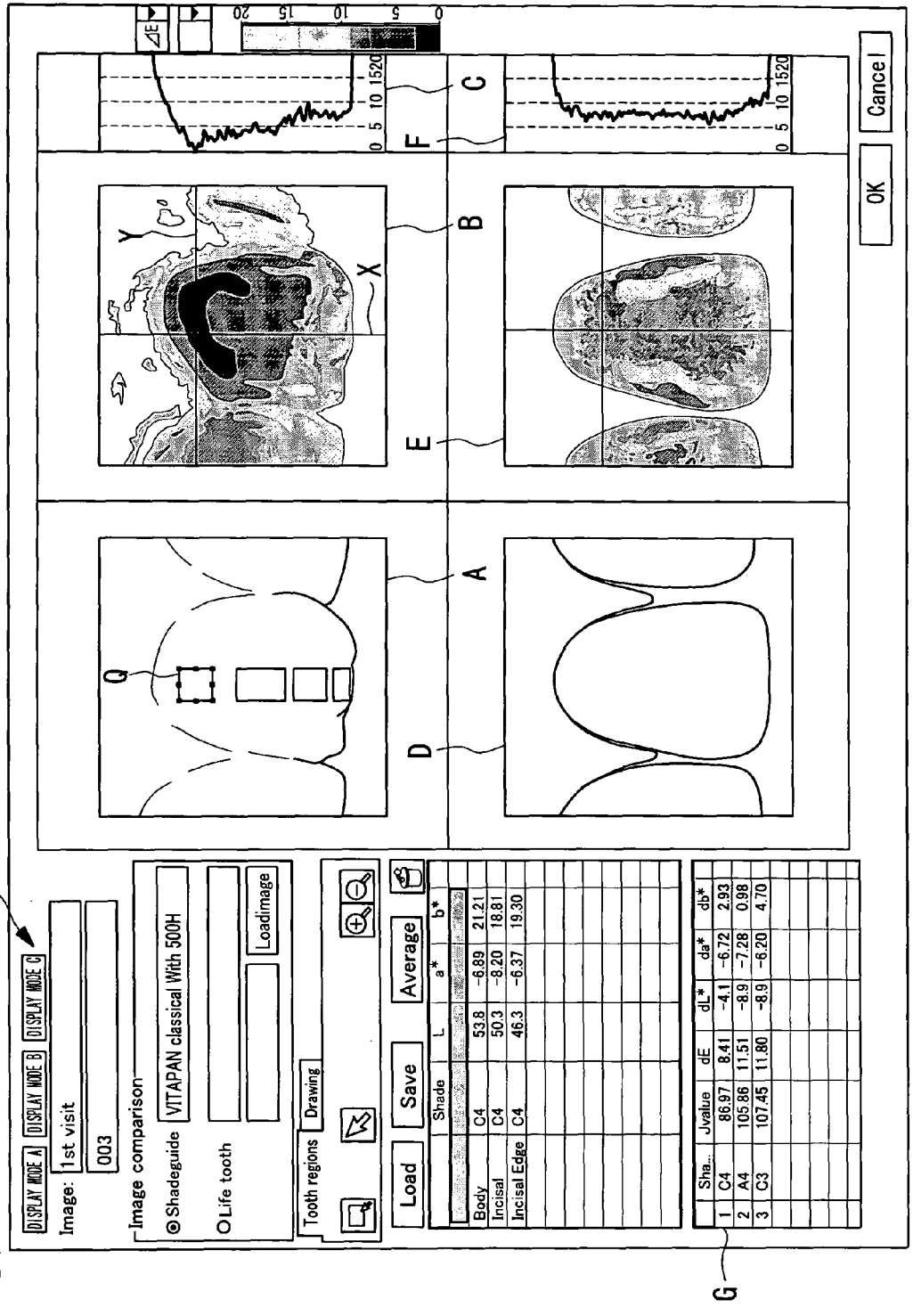
FIG. 13 is a diagram showing an example of a display screen.

When the image-display GUI unit 115 receives the RGB image, the L*a*b* chromaticity values of the measurement regions, the shade-guide number, and so on, which are obtained as described above, from the respective units, it displays an image on the display screen 4, as shown in FIG. 13.

As shown in FIG. 13, the image-display GUI unit 115 displays a color image A of the measurement object at the upper middle part of the display screen and displays an L*a*b* chromaticity distribution image B of the measured object to the right of the color image A. More specifically, the image-display GUI unit 115 displays a vertical scanning line Y, which can move up and down, and a horizontal scanning line X, which can move left and right, on the distribution image B, and it displays a color difference distribution as the distribution image B on the basis of the chroma at a reference position specified at the intersection of these scanning lines Y and X.

In addition, the image-display GUI unit 115 displays the variation in color difference along the vertical scanning line Y or the horizontal scanning line X as a line graph C at the top right of the screen. Because the scanning lines Y and X displayed on the distribution image B are designed to be freely movable by the user, every time the scanning line Y or X is scanned, the image-display GUI unit 115 sends positional information of these scanning lines Y and X after scanning to the difference calculating unit 130 and again calculates the differences $\Delta E$, $\Delta L^*$, $\Delta a^*$, and $\Delta b^*$ in chromaticity values of the tooth on the basis of the intersection of the scanning lines Y and X for each pixel. The image-display GUI unit 115 then obtains a color-difference distribution from the difference calculating unit 130 on the basis of the reference position after scanning and quickly displays this information.

On the color image A, the image-display GUI unit 115 displays the plurality of measurement regions defined in the measurement-region defining processing performed in the determination computing unit 81 (see FIG. 4). Here, when any one region Q of the plurality of measurement regions is specified by the user, such as a dentist, a color image D of the shade guide selected as the one closest to the color of the specified measurement region Q is displayed at the bottom center of the screen, and its $L^*a^*b^*$ chromaticity distribution image E is displayed to the right of the color image D. The image-display GUI unit 115 allows the difference calculating unit 130 to calculate the differences $\Delta E$, $\Delta L^*$, $\Delta a^*$, and $\Delta b^*$ in chromaticity of the shade guide for each pixel on the basis of the chromaticity of the tooth at the intersection of the scanning lines X and Y displayed on the distribution image B and displays the calculated color-difference distribution of the shade guide on the distribution image E.

A vertical scanning line Y and a horizontal scanning line X are also shown in this distribution image E, similarly to the distribution image B, and the image-display GUI unit 115 also displays the variation in color difference along the vertical scanning line Y or the horizontal scanning line X as a line graph F at the bottom right of the screen.

At the bottom left of the screen, the image-display GUI unit 115 displays, in the form of a list, information G about the selected shade guide corresponding to the measurement region Q described above. Here, the three shade-guide numbers selected by the shade-guide selection processing performed in the determination computing unit 81 shown in FIG. 4 are displayed in increasing order of spectrum-determining value (J value). Furthermore, the image-display GUI unit 115 displays the spectrum-determining value (J value) and the differences $\Delta E$, $\Delta L^*$, $\Delta a^*$, and $\Delta b^*$ between the chromaticity values of the tooth and the chromaticity values of the shade guide for each shade-guide number.

At the top left of the screen, the image-display GUI unit 115 displays mode-switching buttons H which allow the display mode to be changed. When these mode-switching buttons H are selected, the image-display GUI unit 115 changes the display screen to the screen shown in FIG. 14.

Figure 14:
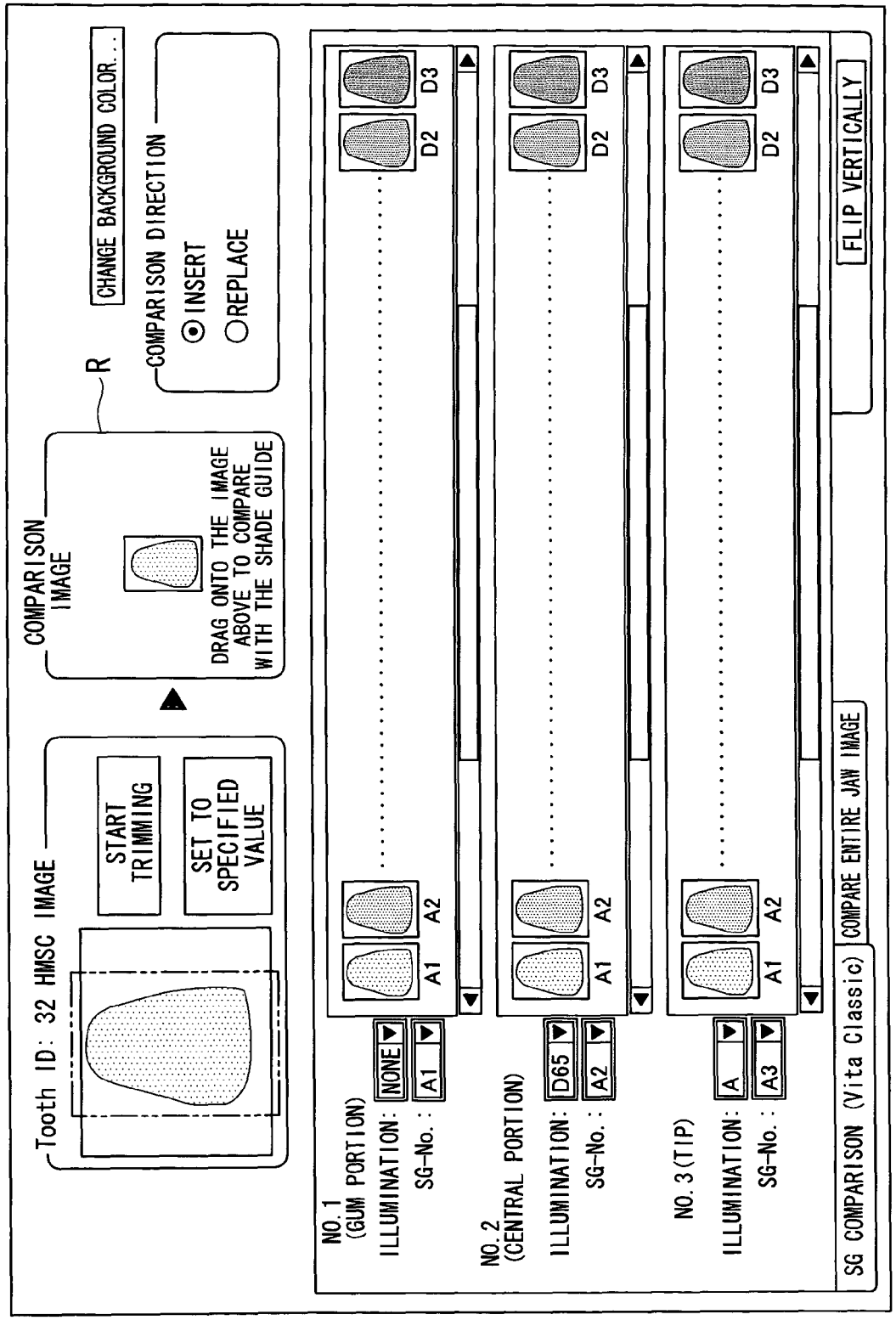
FIG. 14 is a diagram showing an example of a display screen.

As shown in FIG. 14, the image-display GUI unit 115 displays a color image of the tooth being measured close to the top left of the screen. At the bottom center of the screen, the image-display GUI unit 115 displays, in the form of a list, a color image of the shade guides under predetermined illumination light and also displays the shade-guide numbers underneath.

In FIG. 14, "none", "D65", and "A" are selected as the illumination light sources. Here, "none" corresponds to a case where merely the spectral reflectance itself is displayed. The system is designed such that the illumination light can be freely changed using pull-down menus. Accordingly, the user can easily select the desired illumination light and can check for color matching with the shade guide under the desired illumination light. The shade-guide number selected from the available shade guides in the shade-guide selection processing performed in the shade-guide-number determining unit 80 shown in FIG. 4 is indicated by "SG-No" to the left of each shade-guide image.

At the top center of the screen, the image-display GUI unit 115 displays a comparison region R for displaying the vital tooth being measured and a predetermined shade guide adjacent to each other so as to facilitate comparison of the color of the vital tooth being measured and the color of the shade guide. When comparing a vital tooth and a shade guide, close comparison of the colors is difficult if they are displayed at separate location on the screen; the comparison region R is provided to eliminate such a problem.

For example, when the shade guide to be compared is moved from among the shade guides displayed on the screen to the comparison region R by a user input operation such as drag and drop, the image-display GUI unit 115 sends the shade-guide number moved to the comparison region R to the image combining unit 116. Accordingly, image combining processing is carried out by the image combining unit 116 to display on the comparison region R a single combined image in which a part of the vital tooth and a part of the shade guide are displayed adjacent to each other.

The image combining unit 116 according to this embodiment will now be described in detail.

Figure 15:
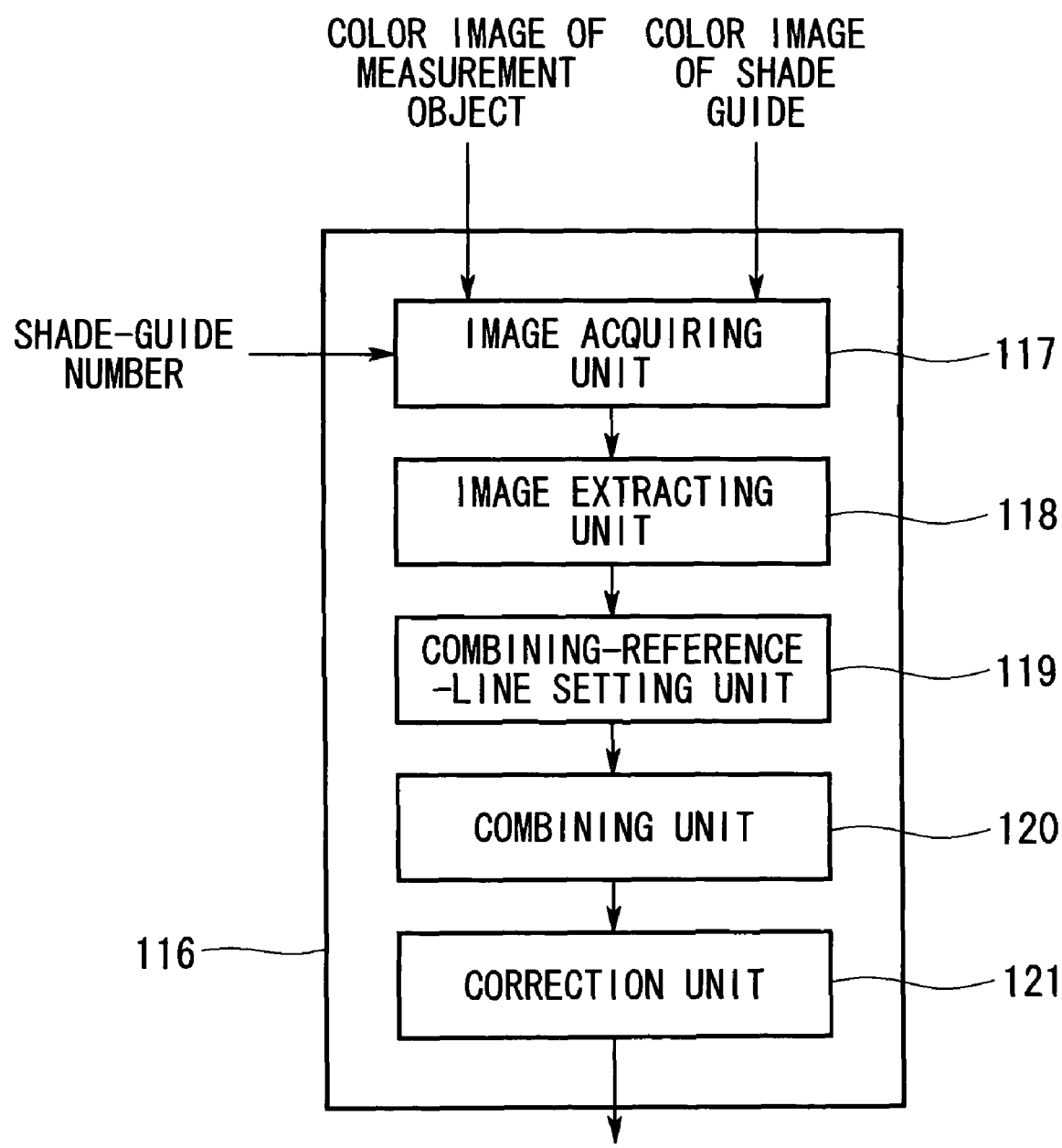
FIG. 15 is a block diagram showing, in outline, the configuration of an image combining unit illustrated in FIG. 4.

As shown in FIG. 15, the image combining unit 116 includes an image acquiring unit 117, an image extracting unit 118, a combining-reference-line setting unit 119, a combining unit 120, and a correction unit 121.

In the image combining unit 116 having such a configuration, a shade-guide number from the image-display GUI unit 115 is input to the image acquiring unit 117. The image acquiring unit 117 acquires a color image (second acquired image) of a shade guide specified by the input shade-guide number from the shade-guide reference-image-data storage unit 82 in the shade-guide-number determining unit 80.

Furthermore, the image acquiring unit 117 acquires a color image (first acquired image) of the vital tooth to be measured from the color-image-generating processor 112. The color image of the shade guide and the color image of the vital tooth to be measured, acquired as described above, are sent to the image extracting unit 118. The image extracting unit 118 extracts a region of the vital tooth (hereinafter referred to as "measurement-object image") from the color image of the vital tooth to be measured and extracts a part of the shade guide, i.e., a part corresponding to the vital tooth (hereinafter referred to as "comparison-object image"), from the color image of the shade guide.

Here, as a method for extracting the measurement-object image and the comparison-object image, the above-described methods used in the determination computing unit 81, that is, "vital-tooth-region specifying method 1", "vital-tooth-region specifying method 2", or the like can be used. Alternatively, for example, both images may be temporarily displayed on the monitor (display device) 4, and the region may be specified by the user. After extracting the measurement-object image and the comparison-object image, the image extracting unit 118 sends this information to the combining-reference-line setting unit 119.

Figure 16:
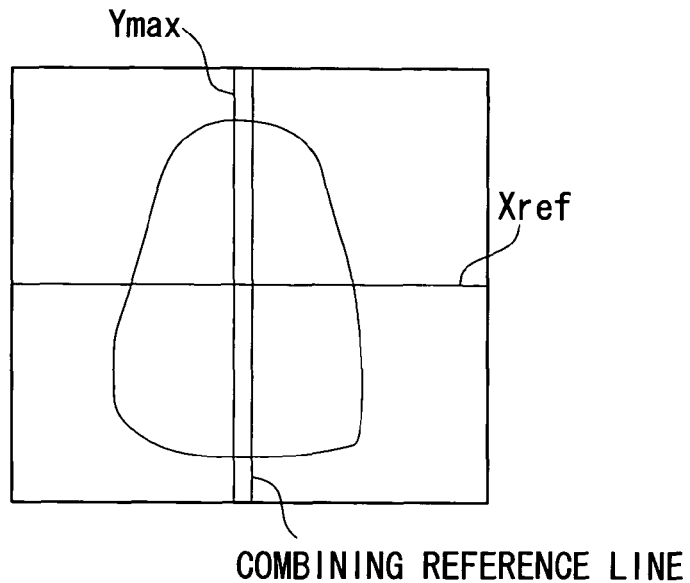
FIG. 16 is a view for explaining a procedure for defining a combining reference line.

The combining-reference-line setting unit 119 sets a combining reference line, which is used as a reference when the measurement-object image and the comparison-object image extracted by the image extracting unit 118 are combined. The combining-reference-line setting unit 119 sets a line, for example, that passes through the center of gravity of the measurement-object image and that is parallel to the vertical axis direction, i.e., the longitudinal direction, as the combining reference line on the measurement-object image. Similarly, the combining-reference-line setting unit 119 sets a line that passes through the center of gravity of the comparison-object image and that is parallel to the vertical axis direction as the combining reference line on the comparison-object image. More specifically, as shown in FIG. 16, a line Ymax having the maximum length in the vertical axis direction is set, and a line Xref that passes through the midpoint of the line Ymax and that is perpendicular to the line Ymax is set. Furthermore, the midpoint of this line Xref is determined, and a line that passes through this midpoint and that is parallel to the line Ymax is set as the combining reference line.

After setting the combining reference line in accordance with the above procedure, the combining-reference-line setting unit 119 sends the measurement-object image and the comparison-object image, in which the combining reference line has been set, to the combining unit 120.

The combining unit 120 combines the measurement-object image and the comparison-object image along the combining reference line. More specifically, the measurement-object image is divided into two parts along the combining reference line, and the comparison-object image is divided into two parts along the combining reference line. Thereafter, the left part of the measurement-object image obtained after division is joined with the right part of the comparison-object image obtained after division to form a combined image. In this case, these images are preferably joined such that the midpoints of the combining reference line are aligned with each other.

Figure 17:
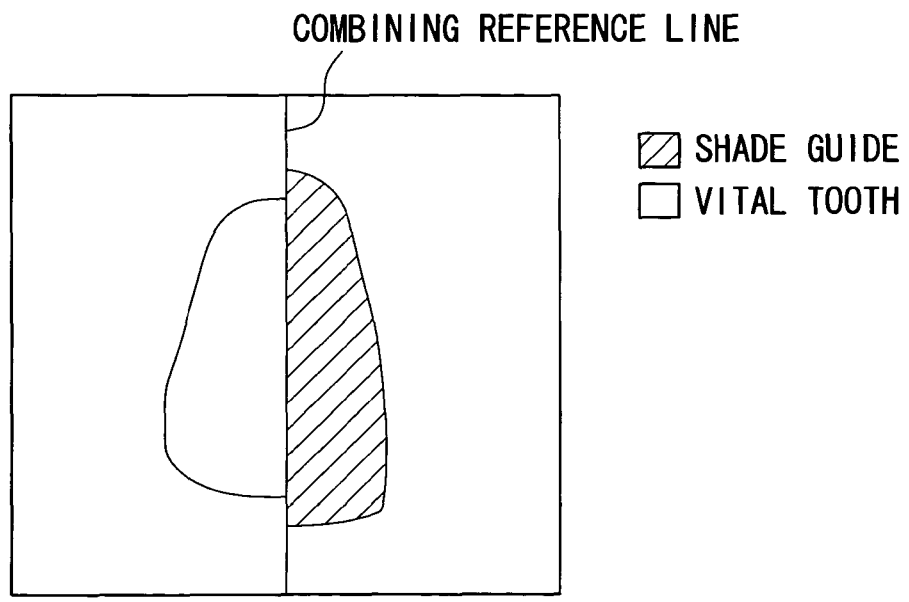
FIG. 17 is a view showing an example of a combined image prepared by a combining unit.

As a result, as shown in FIG. 17, a combined image in which the left half of the measurement-object image and the right half of the comparison-object image are joined is formed. The combining unit 120 sends this combined image to the correction unit 121. The correction unit 121 determines whether or not the outlines on the combining reference line are aligned in the combined image. When the outlines are not aligned, at least one of the measurement-object image and the comparison-object image is corrected to align the outlines.

Figure 18:
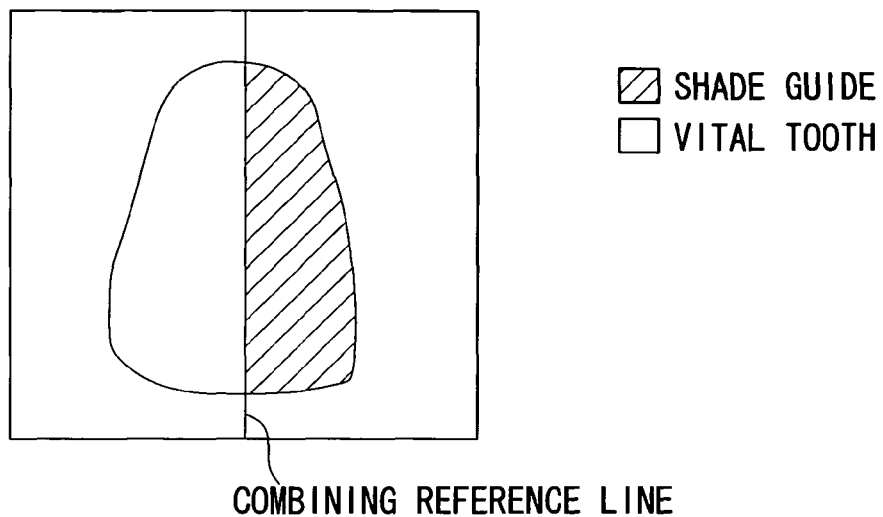
FIG. 18 is a view showing an example of a combined image after correction by a correction unit.

For example, the outlines are aligned by enlarging or reducing either of the images or both images. In such a case, the enlargement/reduction ratio in the vertical axis direction is preferably the same as that in the horizontal axis direction, but it may be different from that in the horizontal axis direction. By performing such a correction, as shown in FIG. 18, the outlines on the combining reference line are aligned to form a natural combined image. The combined image after correction is sent from the correction unit 121 to the image-display GUI unit 115.

After receiving the combined image from the correction unit 121, the image-display GUI unit 115 displays the combined image on the monitor 4. More specifically, the image-display GUI unit 115 displays the combined image on the comparison region R shown in FIG. 14.

The image-display GUI unit 115 also displays a combining reference line (combining-reference-line shifting unit) on the combined image displayed on the comparison region R. This combining reference line is designed so that its position can be freely adjusted with a mouse or the like. When a shift in the position of the combining reference line is instructed, the combining-reference-line setting unit 119 sets a shifted combining reference line on the basis of the direction. By shifting this combining reference line in the horizontal direction, the user can freely change the display ratio of the vital tooth to the shade guide.

Update processing of the combined image in the case where the combining reference line is shifted by the user will now be described in detail. In the description below, a combined image displayed on the comparison region R is defined as an initial combined image, and the combining reference line on the initial combined image is defined as an initial combining reference line.

Figure 19:
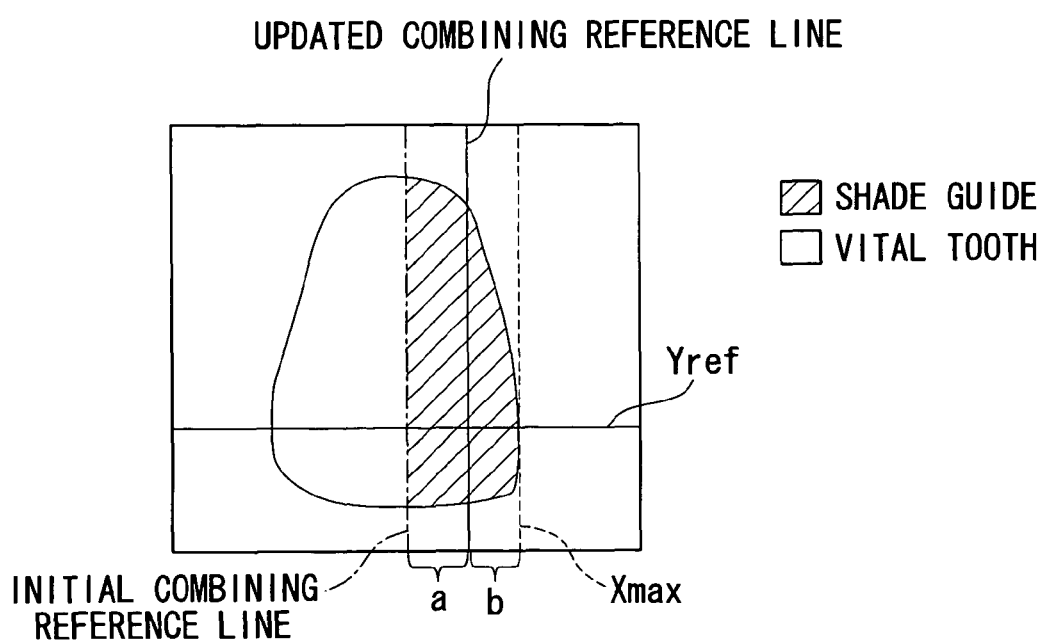
FIG. 19 is a view for explaining a procedure for redefining a combining reference line in the case where the previous combining reference line is moved by a user.

For example, in the initial combined image displayed on the comparison region R in FIG. 14, when the combining reference line is shifted to the right side by the user, as shown in FIG. 19, information about the amount of shift of the combining reference line is sent from the image-display GUI unit 115 to the image combining unit 116. Accordingly, the combining-reference-line setting unit 119 can understand the position where the updated combining reference line is set on the initial combined image.

The combining-reference-line setting unit 119 first determines a line Xmax that passes through the right end of the outline of the initial combined image and that is parallel to the initial combining reference line, and then determines a line Yref that passes through the right end and that is perpendicular to the initial combining reference line. The combining-reference-line setting unit 119 then determines a division ratio a:b defined by dividing the length of the line Yref disposed between the initial combining reference line and the line Xmax by the updated combining reference line.

After determining the division ratio a:b as described above, the combining-reference-line setting unit 119 sets a new combining reference line dividing the measurement-object image and the comparison-object image obtained from the image extracting unit 118 in the initial image combining processing at the same division ratio as that described above and outputs the measurement-object image and the comparison-object image, in which the new combining reference line is set, to the combining unit 120. Combining is then performed by the combining unit 120 on the basis of the new combining reference line to form a new combined image. Furthermore, the new combined image is corrected by the correction unit 121. The corrected combined image is then sent to the image-display GUI unit 115. The image-display GUI unit 115 displays the new combined image received from the correction unit 121 on the comparison region R of the monitor 4. Thus, the new combined image based on the updated combining reference line is shown to the user.

As described above, according to the dental colorimetry system of this embodiment, a combined image is formed by joining a divided measurement-object image prepared by dividing a measurement-object image along the combining reference line with a divided comparison-object image prepared by dividing a comparison-object image along the combining reference line, and this combined image is shown to the user. Accordingly, the user can compare the color of the vital tooth with the color of the shade guide very easily.

Furthermore, in the combined image, the combining reference line can be shifted by the user. Accordingly, by shifting this combining reference line, the user can change the area ratio of the measurement-object image to the comparison-object image in the combined image and freely change the position at which the color is compared.

Furthermore, since the shade guide used in the color comparison can also be changed, the user can freely select a desired shade-guide number as the comparison object. Accordingly, since the combined image based on the desired shade guide and the vital tooth can be displayed, it is possible to compare the color of the vital tooth with the colors of various shade guides.

In the embodiment described above, the procedure for setting a combining reference line by the combining-reference-line setting unit 119 is merely an example, and the procedure for setting a combining reference line is not limited to this example. For example, combining reference lines may be set along the vertical axis direction at positions of the measurement-object image and the comparison-object image at which the length in the vertical axis direction is the maximum.

Figure 20:
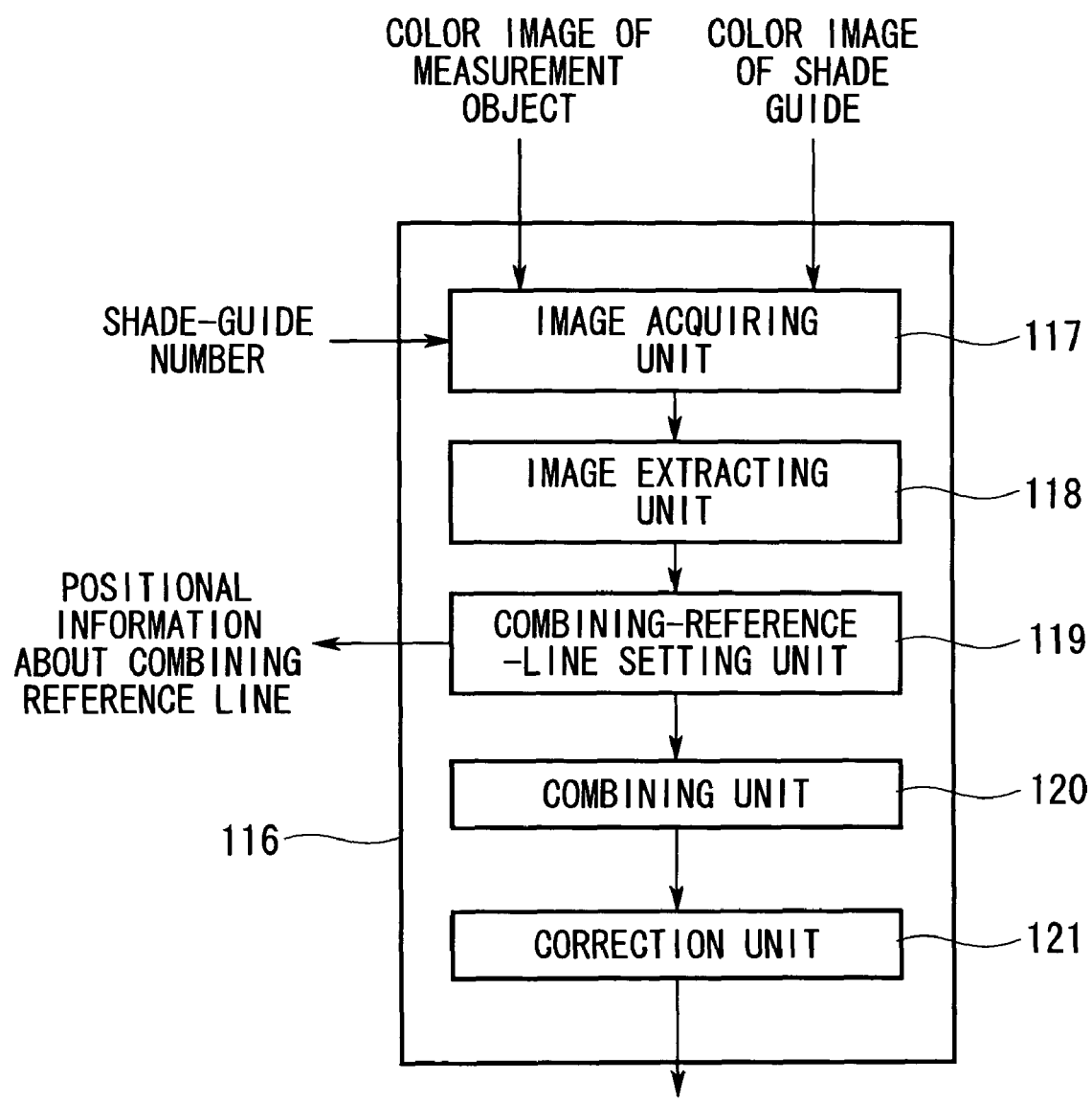
FIG. 20 is a view for explaining the operation of a combining-reference-line setting unit shown in FIG. 15.

Furthermore, the chroma value near the combining reference line may be calculated in each of the vital tooth and the shade guide, and the calculation results may be displayed as numerical data on the same screen. More specifically, as shown in FIG. 20, when the position of the combining reference line is shifted in the combining-reference-line setting unit 119, the positional information about the shifted combining reference line is sent from the combining-reference-line setting unit 119 to the chroma-value computing unit 73. Consequently, the predetermined areas are reset to positions corresponding to the shifted combining reference line. Subsequently, the chroma-value computing unit 73 again calculates, from the spectrum of the object, the averages of the L*a*b* chromaticity values in the predetermined areas after the shift and outputs them to the image-display GUI unit 115 and the difference calculating unit 130.

Furthermore, the difference calculating unit 130 may also calculate the differences between the chromaticity values of the vital tooth and the chromaticity values of the shade guide on the basis of the averages of the L*a*b* chromaticity values in the predetermined areas after the shift, and the differences may also be displayed.

In the above embodiment, a description has been made of the case where the measurement-object image and the comparison-object image are divided on the basis of a combining reference line, but the division may be performed on the entire image. For example, by extending the combining reference line set on the measurement-object image, the combining reference line may be set on the entire color image of the vital tooth from which the image of the measurement object is acquired, and the color image of the vital tooth may be divided into two image pieces along this combining reference line. Similarly, regarding the shade guide image from which the image of the comparison object is acquired, the entire image may be divided into two image pieces on the basis of the combining reference line. By joining these image pieces, it is possible to form a combined image including information about not only the vital tooth, which is the measurement object, and the shade guide, which is the comparison object, but also the background such as the gum.

In FIG. 14, the case where a single combining reference line is set in the vertical axis direction has been described. Alternatively, the combining reference line may be set in the horizontal axis direction, and the number of combining reference lines may be freely set in the vertical axis direction and the horizontal axis direction.

Figure 21:
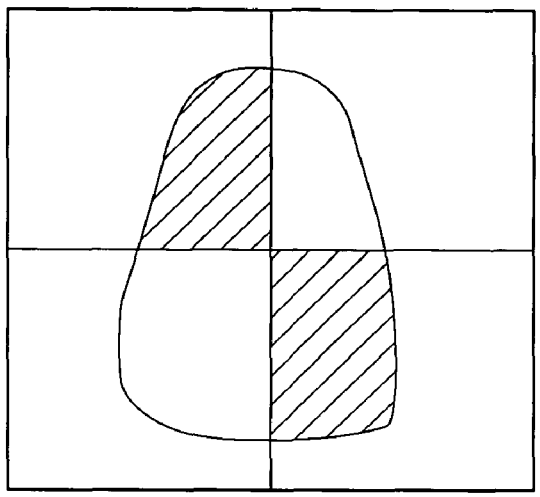
FIG. 21 is a view showing a combined image when the number of vertical combining reference lines is one and the number of horizontal combining reference lines is one.
Figure 22:
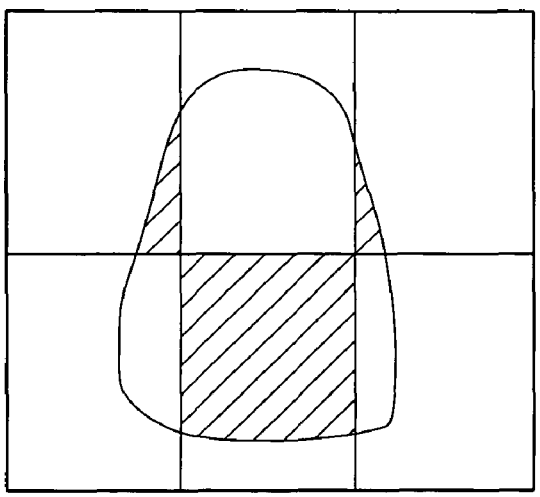
FIG. 22 is a view showing a combined image when the number of vertical combining reference lines is two and the number of horizontal combining reference lines is one.
Figure 23:
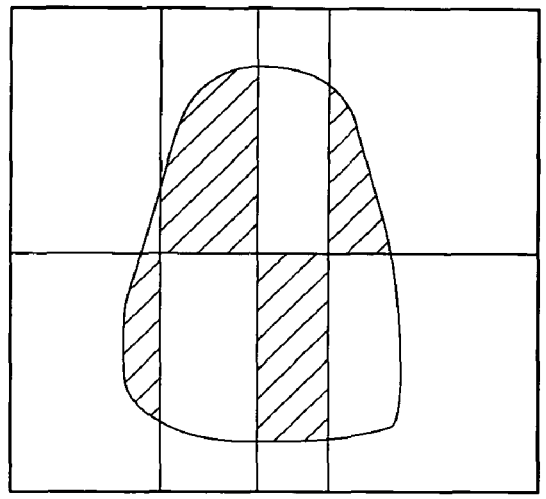
FIG. 23 is a view showing a combined image when the number of vertical combining reference lines is three and the number of horizontal combining reference lines is one.
Figure 24:
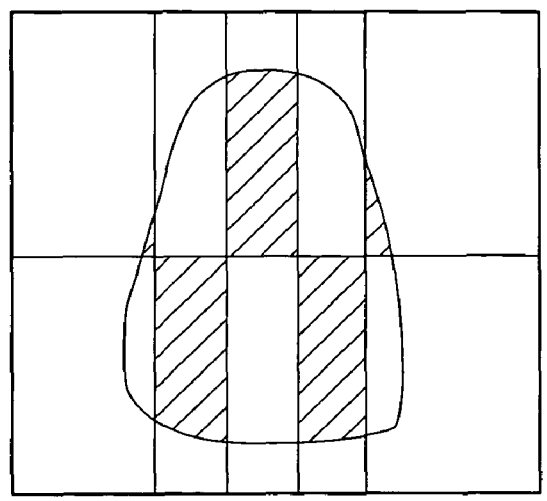
FIG. 24 is a view showing a combined image when the number of vertical combining reference lines is four and the number of horizontal combining reference lines is one.

For example, as shown in FIG. 21, when the number of vertical combining reference lines is one and the number of horizontal combining reference lines is one, a combined image can be formed by joining four image pieces. Similarly, FIG. 22 shows a combined image in which the number of vertical combining reference lines is two and the number of horizontal combining reference lines is one. FIG. 23 shows a combined image in which the number of vertical combining reference lines is three and the number of horizontal combining reference lines is one. FIG. 24 shows a combined image in which the number of vertical combining reference lines is four and the number of horizontal combining reference lines is one.

Also, in these combined images in which a plurality of combining reference lines are set, each of the combining reference lines can be shifted by the user.

Furthermore, the number of shade guides that can be compared with a vital tooth at one time is not limited to one. The system may be designed so that a plurality of shade guides are compared with the vital tooth at one time, and plural types of shade guide may be displayed so as to be adjacent to the vital tooth. For example, in FIG. 16, in the four divided regions, a part of a shade guide may be displayed on the upper left, another shade guide that is different from the upper left shade guide may be displayed on the lower left, and the vital tooth may be displayed in the two right regions. Similarly, the system may be designed so that a shade guide is compared with a plurality of vital teeth at one time.

What is claimed is:

1. An image combining apparatus for forming an image by combining a first multispectral acquired image containing an image of a measurement object and a second multispectral acquired image containing an image of a comparison object to be compared with the measurement object, comprising:

an image extracting unit for specifying: (i) an outline of a measurement-object image by extracting a region having a combination of signal values projected onto a plane representing a characteristic of the measured object in an n-dimensional space from the respective combination of signal values of n wavelength bands that forms the first multispectral acquired image, and (ii) an outline of a comparison-object image by extracting a region having a combination of signal values projected onto a plane representing a characteristic of the comparison object in an n-dimensional space from the respective combination of signal values of n wavelength bands that forms the second multispectral acquired image, where n is four or more;

a combining-reference-line setting unit for setting a combining reference line on each of the measurement-object image and the comparison-object image;

a combining unit for combining the measurement-object image and the comparison-object image such that a part of the measurement-object image and a part of the comparison-object image are joined along the combining reference lines to form a combined image; and a correction unit for correcting at least one of the measurement-object image and the comparison-object image so as to align outlines thereof, when the correction unit determines that the outline of the measurement-object image and the outline of the comparison-object image, specified by the image extracting unit, are not aligned on the combining reference lines in the combined image.

2. The image combining apparatus according to claim 1, wherein the combining-reference-line setting unit sets a line that passes through a center of gravity of the measurement-object image as the combining reference line on the measurement-object image and sets a line that passes through a center of gravity of the comparison-object image as the combining reference line on the comparison-object image.

3. The image combining apparatus according to claim 1, wherein the combining-reference-line setting unit sets the combining reference line at a position where a length of the measurement-object image in the vertical axis direction is maximum on the measurement-object image along a vertical axis direction and sets the combining reference line at a position where a length of the comparison-object image in the vertical axis direction is maximum on the comparison-object image along the vertical axis direction.

4. The image combining apparatus according to claim 1, further comprising a combining-reference-line shifting unit for shifting the combining reference line in the combined image using an external device.

5. The image combining apparatus according to claim 1, wherein the correction unit reduces or enlarges at least one of the measurement-object image and the comparison-object image.

6. The image combining apparatus according to claim 5, wherein the measurement object is a vital tooth and the comparison object is a shade guide.

7. A dental colorimetry system comprising:
the image combining apparatus according to claim 1;
a chroma-value computing unit for computing chromaticity values near the combining reference line in the measurement-object image;
a difference calculating unit for calculating differences between the chromaticity values near the combining reference line of the measurement-object image and chromaticity values near the combining reference line of the comparison-object image; and
a display control unit for displaying at least one of the chromaticity values near the combining reference line of the measurement-object image, the chromaticity values near the combining reference line of the comparison-object image, and the differences in the chromaticity values on a screen displaying the combined image.

8. A dental colorimetry system comprising:
an image-acquisition apparatus configured to acquire an oral-cavity image; and
a dental colorimetry apparatus including an image combining apparatus for forming an image by combining a first multispectral acquired image containing an image of a measurement object acquired with the image-acquisition apparatus and a second multispectral acquired image containing an image of a comparison object to be compared with the measurement object,
wherein the image combining apparatus includes:
an image extracting unit for specifying:
(i) an outline of a measurement-object image by extracting a region having a combination of signal values projected onto a plane representing a characteristic of the measured object in an n-dimensional space from the respective combination of signal values of n wavelength bands that forms the first multispectral acquired image, and (ii) an outline of a comparison-object image by extracting a region having a combination of signal values projected onto a plane representing a characteristic of the comparison object in an n-dimensional space from the respective combination of signal values of n wavelength bands that forms the second multispectral acquired image, where n is four or more;
a combining-reference-line setting unit for setting a combining reference line on each of the measurement-object image and the comparison-object image;
a combining unit for combining the measurement-object image and the comparison-object image such that a part of the measurement-object image and a part of the comparison-object image are joined along the combining reference lines to form a combined image; and
a correction unit for correcting at least one of the measurement-object image and the comparison-object image so as to align outlines thereof, when the correction unit determines that the outline of the measurement-object image and the outline of the comparison-object image, specified by the image extracting unit, are not aligned on the combining reference lines in the combined image.

9. An image combining method for forming an image by combining a first multispectral acquired image containing an image of a measurement object and a second multispectral acquired image containing an image of a comparison object to be compared with the measurement object, comprising:
specifying: (i) an outline of a measurement-object image by extracting a region having a combination of signal values projected onto a plane representing a characteristic of the measured object in an n-dimensional space from the respective combination of signal values of n wavelength bands that forms the first multispectral acquired image, and (ii) an outline of a comparison-object image by extracting a region having a combination of signal values projected onto a plane representing the characteristic of the comparison object in an n-dimensional space from the respective combination of signal values of n wavelength bands that forms the second multispectral acquired image, where n is four or more;
setting a combining reference line on each of the measurement-object image and the comparison-object image;
combining the measurement-object image and the comparison-object image such that a part of the measurement-object image and a part of the comparison-object image are joined along the combining reference lines to form a combined image; and
correcting at least one of the measurement-object image and the comparison-object image so as to align their outlines, when it is determined that the specified outline of the measurement-object image and the specified outline of the comparison-object image are not aligned on the combining reference lines in the combined image.

10. A non-transitory computer readable medium having an image combining program stored thereon which controls a computer to form a combined image by combining a first acquired multispectral image containing an image of a measurement object and a second multispectral acquired image containing an image of a comparison object to be compared with the measurement object, the image combining program causing the computer to execute functions comprising:
image extracting processing for specifying:
(i) an outline of a measurement-object image by extracting a region having a combination of signal values projected onto a plane representing a characteristic of the measured object in an n-dimensional space from the respective combination of signal values of n wavelength bands that forms the first multispectral acquired image, and (ii) an outline of a comparison-object image by extracting a region having a combination of signal values projected onto a plane representing a characteristic of the comparison object in an n-dimensional space from the respective combination of signal values of n wavelength bands that forms the second multispectral acquired image, where n is four or more;
combining-reference-line setting processing for setting a combining reference line on each of the measurement-object image and the comparison-object image;
combining processing for combining the measurement-object image and the comparison-object image such that a part of the measurement-object image and a part of the comparison-object image are joined along the combining reference lines to form a combined image; and correction processing for correcting at least one of the measurement-object image and the comparison-object image so as to align their outlines, when it is determined that the specified outline of the measurement-object image and the specified outline of the comparison-object image are not aligned on the combining reference lines in the combined image.

11. The computer-readable medium according to claim 10, wherein the combining-reference-line setting processing sets a line that passes through a center of gravity of the measurement-object image as the combining reference line on the measurement-object image and sets a line that passes through a center of gravity of the comparison-object image as the combining reference line on the comparison-object image.

12. The computer-readable medium according to claim 10, wherein the combining-reference-line setting processing sets the combining reference line at a position where a length of the measurement-object image in a vertical axis direction is maximum on the measurement-object image along the vertical axis direction and sets the combining reference line at a position where a length of the comparison-object image in the vertical axis direction is maximum on the comparison-object image along the vertical axis direction.

13. The computer-readable medium according to claim 10, further comprising combining reference line shifting processing for shifting the combining reference line in the combined image using an external device.

14. The computer-readable medium according to claim 10, wherein the correction processing reduces or enlarges at least one of the measurement-object image and the comparison-object image.

15. The computer-readable medium according to claim 14, wherein the measurement object is a vital tooth and the comparison object is a shade guide.

16. A non-transitory computer readable medium having a dental colorimetry program stored thereon which controls a computer to execute functions comprising:

the image combining program according to claim 10;

chroma-value computing processing for computing chromaticity values near the combining reference line in the measurement-object image;

difference calculating processing for calculating differences between the chromaticity values near the combining reference line of the measurement-object image and chromaticity values near the combining reference line of the comparison-object image; and display control processing for displaying at least one of the chromaticity values near the combining reference line of the measurement-object image, the chromaticity values near the combining reference line of the comparison-object image, and the differences in the chromaticity values on a screen displaying the combined image.

17. The image combining apparatus according to claim 1, wherein the combined image comprises half of the measurement-object image and half of the comparison-object image.

18. The dental colorimetry system according to claim 8, wherein the combined image comprises half of the measurement-object image and half of the comparison-object image.

19. The image combining method according to claim 9, wherein the combined image comprises half of the measurement-object image and half of the comparison-object image.

20. The computer-readable medium according to claim 10, wherein the combined image comprises half of the measurement-object image and half of the comparison-object image.

* * * * *